United States Patent
Bonati et al.

(10) Patent No.: US 7,090,680 B2
(45) Date of Patent: Aug. 15, 2006

(54) METHOD FOR REMOVING ORTHOPAEDIC HARDWARE

(76) Inventors: Alfred O. Bonati, 1650 Beach Dr. NE., St. Petersburg, FL (US) 33704; Philip J. Ware, 5395 Idleweist Ct., Spring Hill, FL (US) 34606

( * ) Notice: Subject to any disclaimer, the term of this patent is extended or adjusted under 35 U.S.C. 154(b) by 352 days.

(21) Appl. No.: 10/365,076

(22) Filed: Feb. 12, 2003

(65) Prior Publication Data

US 2004/0158258 A1    Aug. 12, 2004

(51) Int. Cl.
*A61B 17/58* (2006.01)
*A61F 2/00* (2006.01)

(52) U.S. Cl. ...................................................... 606/104
(58) Field of Classification Search ................ 606/53, 606/86, 99, 97, 98, 104; 81/90.5
See application file for complete search history.

(56) References Cited

U.S. PATENT DOCUMENTS

| | | | |
|---|---|---|---|
| 2,634,641 A | 4/1953 | Hodges | |
| 2,669,896 A | 2/1954 | Clough | |
| 2,753,746 A | 2/1956 | Rauner | |
| 3,373,639 A | 3/1968 | Van Dalen et al. | |
| 3,377,893 A | 4/1968 | Shorb | |
| 3,604,487 A | 9/1971 | Gilbert | |
| 5,203,781 A | 4/1993 | Bonati et al. | |
| 5,213,015 A | 5/1993 | Disston, Jr. | |
| 5,241,972 A | 9/1993 | Bonati | |
| 5,269,797 A * | 12/1993 | Bonati et al. ............... | 606/170 |
| 5,290,279 A | 3/1994 | Bonati et al. | |
| 5,357,983 A * | 10/1994 | Mathews ..................... | 128/898 |
| 5,472,426 A | 12/1995 | Bonati et al. | |
| 5,484,440 A | 1/1996 | Allard | |
| 5,649,931 A | 7/1997 | Bryant et al. | |
| 5,667,513 A | 9/1997 | Torrie et al. | |
| 5,895,352 A * | 4/1999 | Kleiner ........................ | 600/206 |
| 5,951,559 A | 9/1999 | Burkhart | |
| 5,976,146 A * | 11/1999 | Ogawa et al. ................ | 606/86 |
| 6,033,406 A * | 3/2000 | Mathews ..................... | 606/61 |
| 6,183,472 B1 | 2/2001 | Lutz | |
| 6,189,422 B1 * | 2/2001 | Stihl ............................ | 81/452 |
| 6,200,322 B1 | 3/2001 | Branch et al. | |
| 6,267,025 B1 * | 7/2001 | Sand et al. .................. | 81/53.2 |
| 6,860,889 B1 * | 3/2005 | Bonati et al. ................ | 606/104 |

\* cited by examiner

*Primary Examiner*—Eduardo C. Robert
*Assistant Examiner*—Anu Ramana

(57) ABSTRACT

A method for gaining access to and removing mechanical fasteners such as pedicle screws. A small arthroscopic incision is made over the location of the fastener. A guide wire is then placed into the incision and attached to the fastener. A series of progressively enlarging dilator tubes are slipped into the incision to progressively enlarge its diameter. A screw extractor tube is placed into the incision, over the largest dilator tube. The screw extractor tube is advanced until its lower extreme surrounds the head of the fastener. The dilator tubes are then removed. At this point, the screw extractor tube holds open the incision and provides access to the fastener through its hollow interior. A specially designed extractor tool is inserted into the screw extractor tube. An arthroscope is preferably also inserted through the screw extractor tube so that the surgeon can visualize the process. Jaws on the end of the extractor tool are clamped to the fastener's head. The extractor tool is then rotated to back out the fastener. Once the fastener is freed from its installed position, the extractor tool withdraws it through the screw extractor tube. Other conventional processes—such as debridement—may then be performed through the screw extractor tube. Finally, the surgeon withdraws the screw extractor tube and closes the small incision.

14 Claims, 24 Drawing Sheets

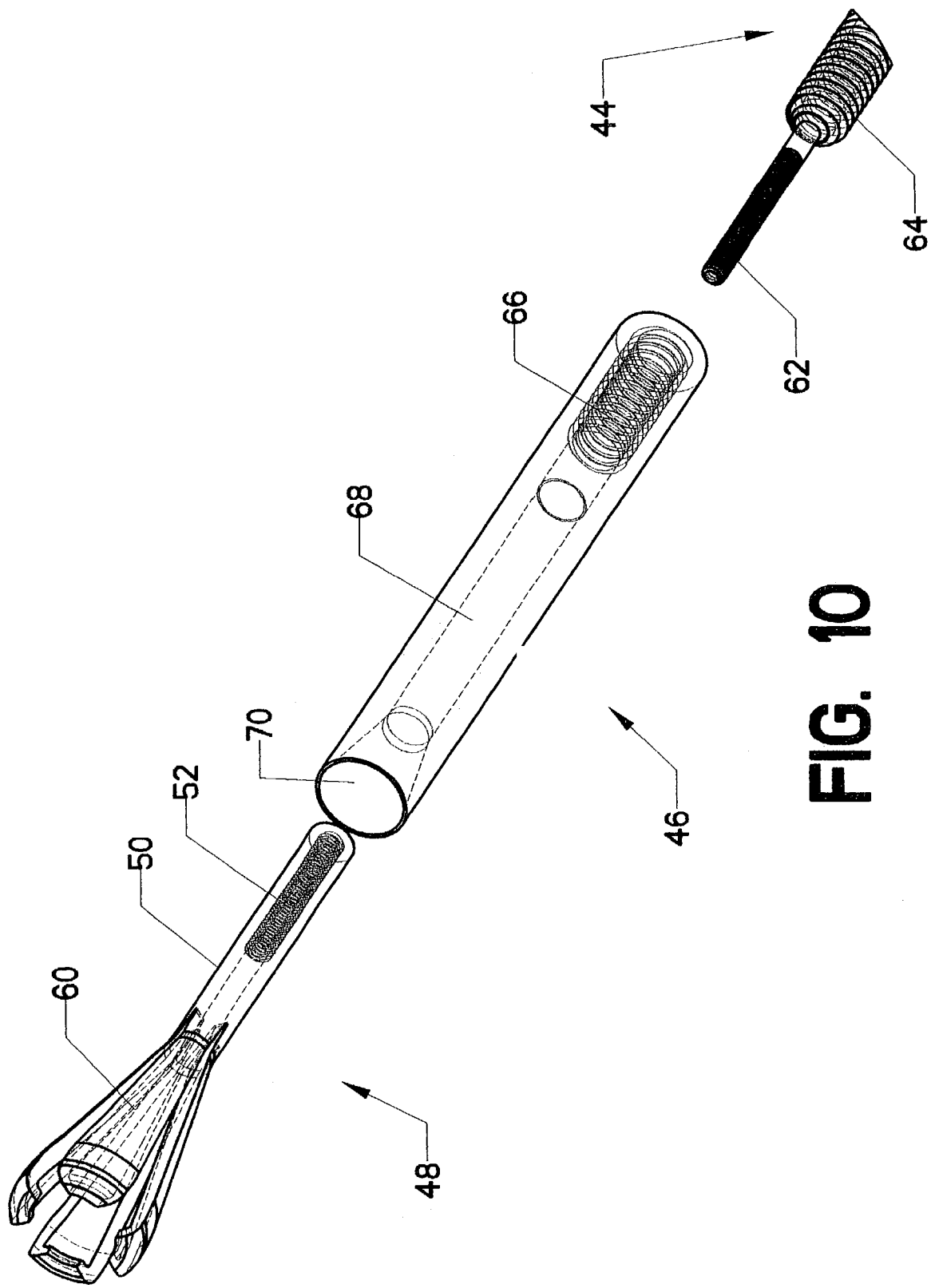

METHOD FOR REMOVING ORTHOPAEDIC HARDWARE

CROSS-REFERENCES TO RELATED APPLICATIONS

This application pertains to subject matter also disclosed in my copending application for the invention entitled "CLAMPING SCREW EXTRACTOR," filed on Oct. 7, 2002, and having application Ser. No. 10/266133.

STATEMENT REGARDING FEDERALLY SPONSORED RESEARCH OR DEVELOPMENT

Not Applicable.

MICROFICHE APPENDIX

Not Applicable

BACKGROUND OF THE INVENTION

1. Field of the Invention

This invention relates to the field of orthopaedic surgery. More specifically, the invention comprises a process for removing orthopaedic hardware while using only a small incision.

2. Description of the Related Art

The field of orthopaedic medicine involves the application of plates and screws to stabilize compromised articulations in the human body. One typical application is stabilization of the lumbar vertebrae after collapse of one or more intervertebral disks. FIG. 1 is an illustration of two lumbar vertebrae 10. Intervertebral disk 11 lies between the two. In this example, instability of the spine has necessitated the joining of the two vertebrae.

It is well known in the art that vertebrae can be joined by bone grafting. However, it is generally necessary to stabilize the position of the two vertebrae for some period in order to allow the joining to occur. Accordingly, plate 12 is attached to the two vertebrae. Typically two plates 12 would be applied, with one lying on each side of the posterior spinous processes. Each plate 12 is pierced by a set of holes, through which pedicle screws 14 are inserted.

In order to install pedicle screws 14, holes must be drilled through the pedicle portions of the two vertebrae. Pedicle screws 14 are then threaded into these holes and tightened. If all goes well, the two vertebrae will eventually fuse together, thereby eliminating any articulation at the joint. The fusing will ideally render the patient asymptomatic, though obviously somewhat less flexible.

The ideal result is not always achieved, however. Those skilled in the art will know that great variations exist in human anatomy. They will also know that the surgeon is unable to fully visualize the structures involved. These factors may lead to imperfect results.

The reader will observe in FIG. 1 that nerve root 20 exits the foramen between the two vertebrae in a position which is close to the lower pedicle screw 14. A portion of this pedicle screw 14 may protrude beyond the surface of the lower vertebra 10 (As the vertebra comprises a highly irregular shape, the hole drilled therethrough may intersect the outer surface at one or more points. A portion of the threaded pedicle screw shaft may thereby be exposed). This portion may rest against nerve root 20, possibly even compressing nerve root 20. In such an event, the patient may experience common neurological symptoms, such as pain or numbness.

After the joint has stabilized, it may be desirable to remove pedicle screw 14 (as well as possibly plate 12). This operation has typically been performed under general anesthesia. A substantial incision is made through the skin 18, and fascia 16, to reveal the spinal column. The muscles and other structures attached to the posterior spinous processes must then be removed in order to expose pedicle screw 14. A wrench is then used to back pedicle screw 14 out of the bone and remove it through the open incision. It is often difficult to determine whether a particular pedicle screw is the source of the neurological symptoms experienced by the patient. As the patient is asleep during the procedure, there is no way to determine if the removal of the screw altered the symptoms until much later.

FIG. 2 shows another common factor in the placement of such hardware. The reader will observe that pedicle screw 14 is angularly displaced from the axial center of the hole through plate 12. This angular displacement is sometimes necessary in order to accommodate the shape of the vertebra. On other occasions, it is simply a result of the imperfect drilling process. Whatever the cause, the angular displacement may necessitate a larger incision since the socket head of the removing device must be aligned with screw head 22.

BRIEF SUMMARY OF THE PRESENT INVENTION

The present invention comprises a method for gaining access to and removing mechanical fasteners such as pedicle screws. A small arthroscopic incision is made over the location of the fastener. A guide wire is then placed into the incision and attached to the fastener. A series of progressively enlarging dilator tubes are slipped into the incision to progressively enlarge its diameter. A screw extractor tube is placed into the incision, over the largest dilator tube. The screw extractor tube is advanced until its lower extreme surrounds the head of the fastener. The dilator tubes are then removed. At this point, the screw extractor tube holds open the incision and provides access to the fastener through its hollow interior.

A specially designed extractor tool is inserted into the screw extractor tube. An arthroscope is preferably also inserted through the screw extractor tube so that the surgeon can visualize the process. Jaws on the end of the extractor tool are clamped to the fastener's head. The extractor tool is then rotated to back out the fastener. Once the fastener is freed from its installed position, the extractor tool withdraws it through the screw extractor tube. Other conventional processes—such as debridement—may then be performed through the screw extractor tube. Finally, the surgeon withdraws the screw extractor tube and closes the small incision.

REFERENCE NUMERALS IN THE DRAWINGS

| 10 | vertebra | 12 | plate |
|---|---|---|---|
| 14 | pedicle screw | 16 | fascia |
| 18 | skin | 20 | nerve root |
| 22 | screw head | 24 | small incision |
| 26 | first dilater tube | 28 | second dilater tube |
| 30 | screw extractor tube | 32 | access cut |
| 34 | insertion curve | 36 | access curve |
| 38 | upper curve | 40 | tenth dilater tube |
| 42 | handle | 44 | shaft |
| 46 | thread sleeve | 48 | collet |
| 50 | insertion cylinder | 52 | threaded bore |
| 54 | jaw | 56 | split |
| 58 | knurled surface | 60 | tapered journal |
| 62 | threaded journal | 64 | threaded journal |
| 66 | threaded bore | 68 | straight bore |
| 70 | tapered bore | 72 | extraction tool |
| 74 | arthroscope | 76 | hollow interior |
| 78 | undercut | 80 | screw head cavity |
| 82 | lumbar region | 84 | guide wire |
| 86 | socket extractor | 88 | large tube |
| 90 | first alternate tube | 92 | second alternate tube |
| 94 | third alternate tube | 96 | shear plane |
| 98 | filleted shear plane | 100 | notch |

DETAILED DESCRIPTION OF THE INVENTION

Figure 1:
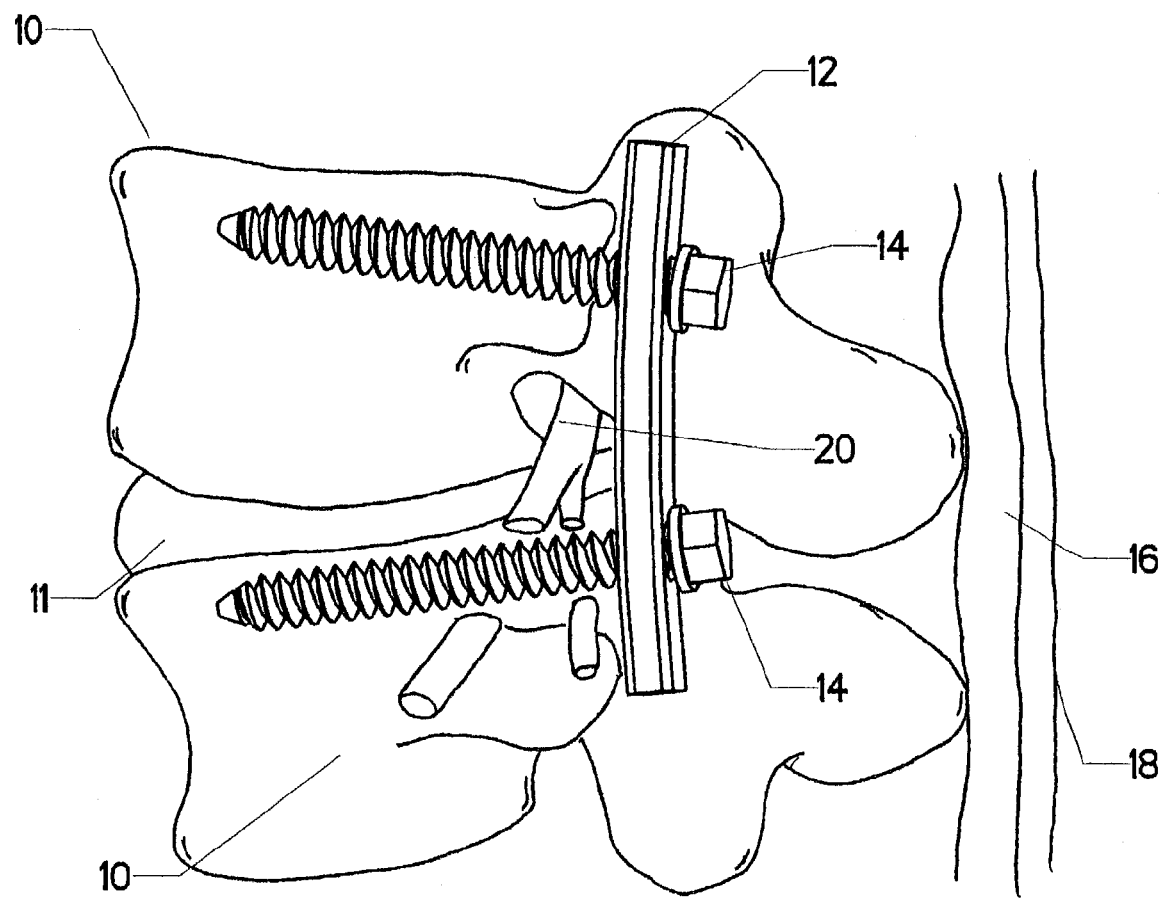
FIG. 1 is an isometric view, showing a prior art plate and pair of pedicle screws.
Figure 2:
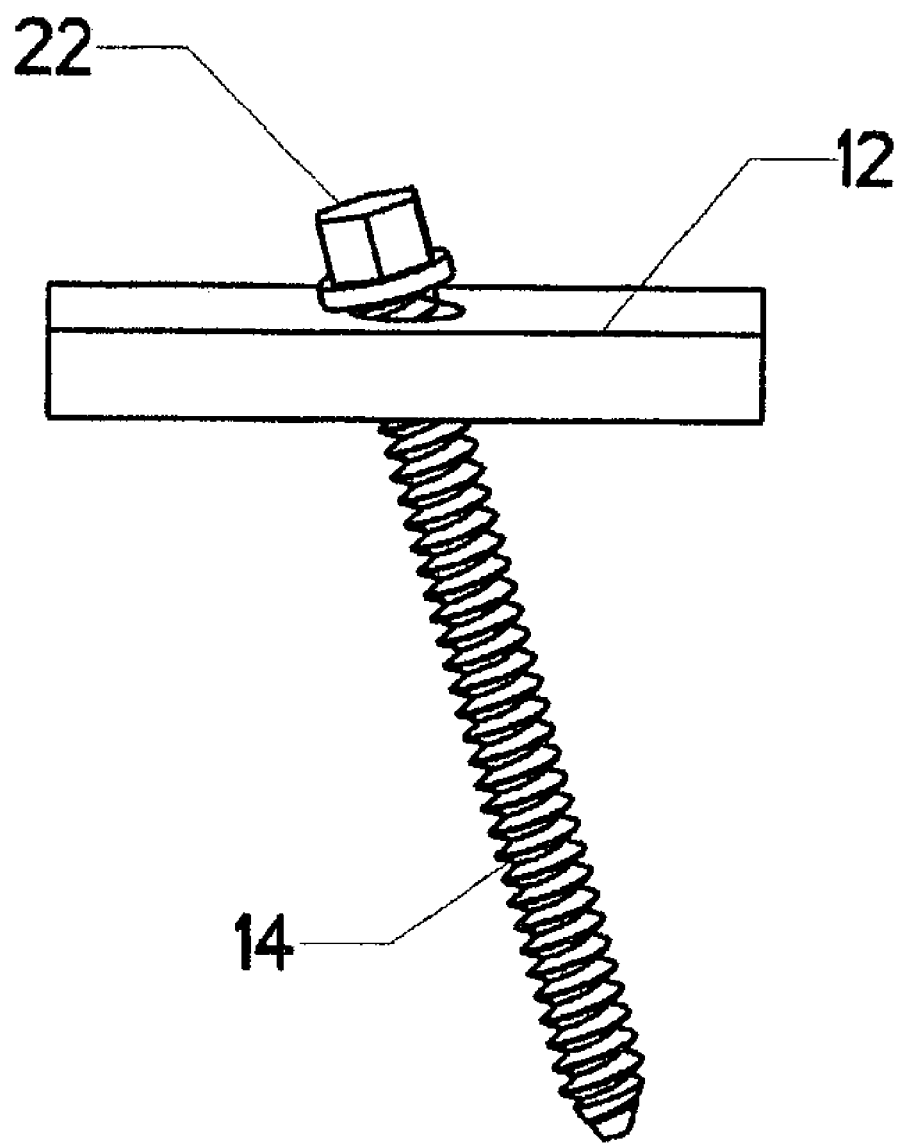
FIG. 2 is an isometric view, showing a pedicle screw.
Figure 3:
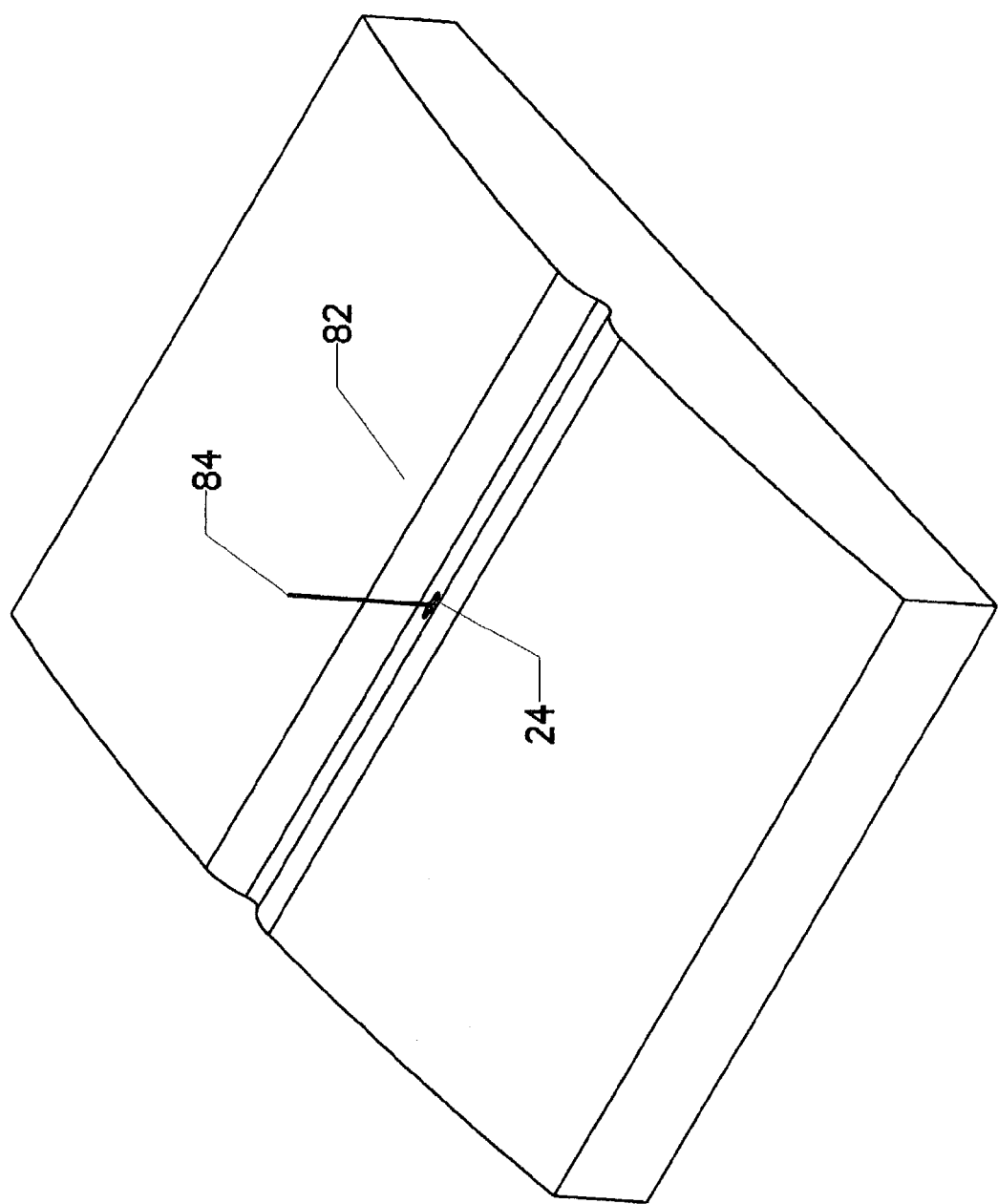
FIG. 3 is an isometric view, showing an initial incision.
Figure 4:
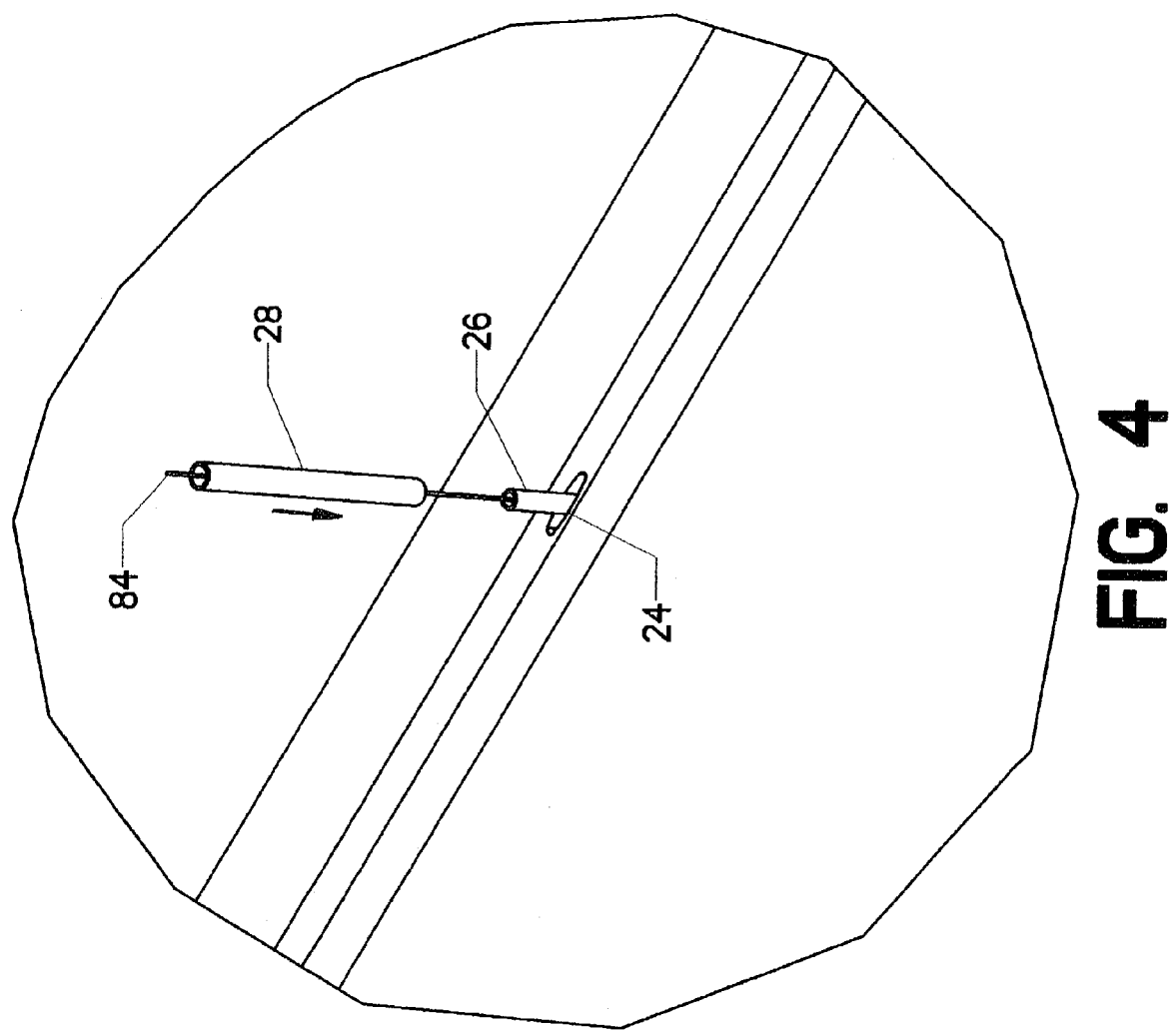
FIG. 4 is an isometric view, showing the installation of successive dilater tubes.

Referring now to FIG. 1, the objective for which the invention was primarily designed is the removal of one or more pedicle screws 14. Radiographic techniques are used to locate the suspicious pedicle screw. Turning now to FIG. 3, small incision 24 is made directly over the pedicle screw. A guide wire 84 is then placed on the screw head, with its free end extending out of the incision as shown. Turning now to FIG. 4, first dilater tube 26 is placed in the incision by slipping it along the guide wire. First dilater tube 26 is a hollow tube having an inner diameter greater than the guide wire. By inserting it into the incision along the guide wire, the incision is dilated slightly. Next, a succession of dilator tubes, each having a slightly larger diameter than its predecessor, is slipped into place within the incision. Second dilator tube 28 is shown in position, ready to be slipped over first dilator tube 26. The incision is thereby incrementally expanded to a diameter of approximately 16 mm. the process of installing the dilator tubes, along with more detailed descriptions of the tubes themselves, is found in U.S. Pat. No. 5,472,426 to Bonati et.al., which is incorporated herein by reference. The succession of dilator tubes can be added without removing any prior dilator tubes. In the alternative, each preceding dilator tube can be removed once it has guided its successor into position (so that there are never more than two dilator tubes in the incision at any one time).

Figure 5:
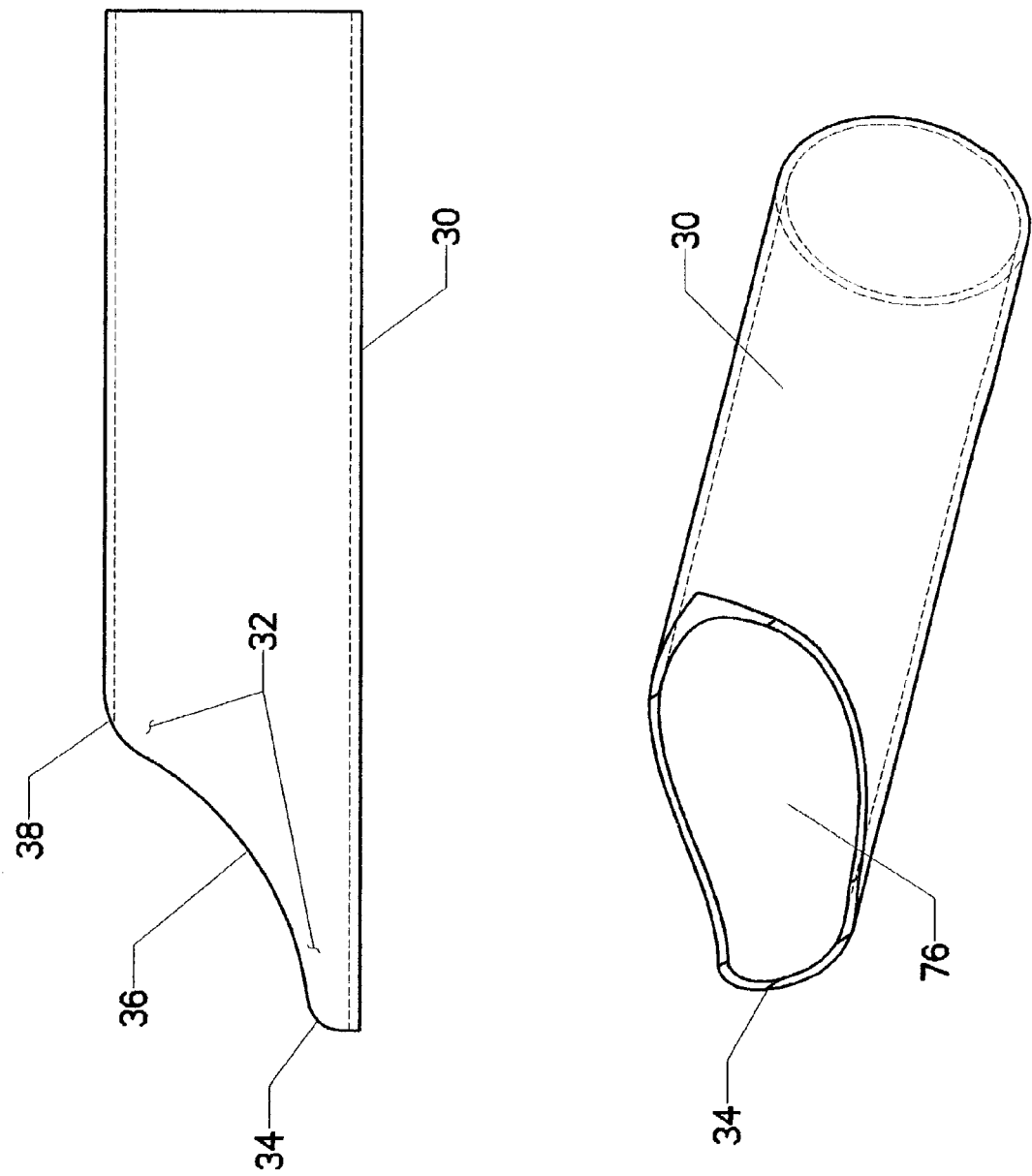
FIG. 5 is an isometric view, showing a screw extractor tube.

The last dilater tube has a specialized design intended to facilitate the screw extraction process. FIG. 5 shows this specialized tube, denoted as screw extractor tube 30. The upper view in FIG. 5 shows screw extractor tube 30 from the side. The reader will observe that a specialized shape is cut into the portion intended to provide access to the incision. Insertion curve 34 extends across the leading portion. Relief curve 36 lies behind this. Finally, upper curve 38 blends into the cylindrical body of the tube. These three curved portions arc referred to collectively as access cut 32.

Figure 6:
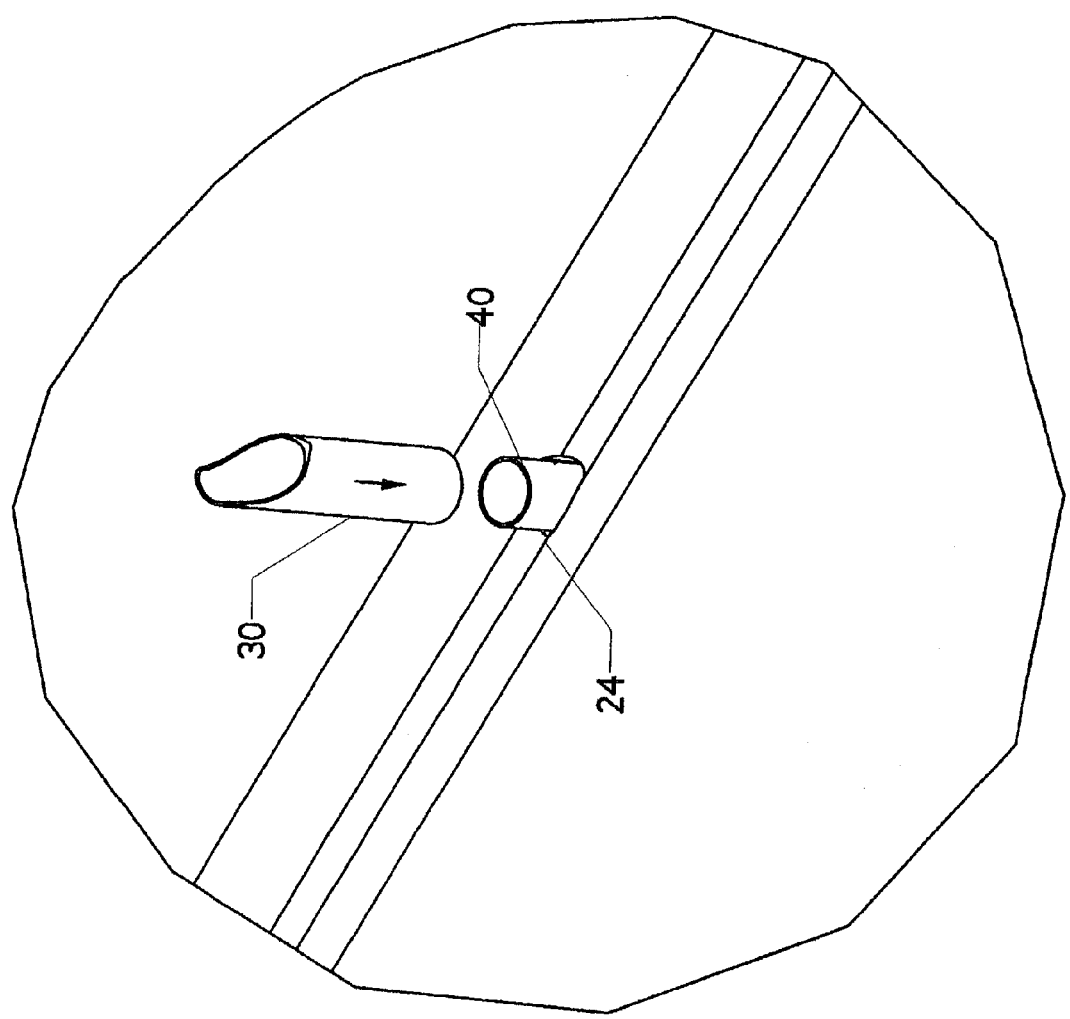
FIG. 6 is an isometric view, showing the installation of a screw extractor tube.

FIG. 6 shows the original incision with tenth dilator tube 40 in place (being the last in a succession often tubes of incrementally expanding diameters). Screw extractor tube 30 operates as an eleventh dilator tube. It is placed over tenth dilator tube 40 and down into the incision. Tenth dilator tube 40 is then removed. Once in position, screw extractor tube 30 provides access to the exposed head portion of the pedicle screw through its hollow interior 76. The number of dilator tubes employed is not critical to the invention—so long as they provide a gradual dilation of the incision.

Thus, using the devices and procedures described, a surgeon can gain access to the pedicle screw by making only a small incision. Such an incision can be made under local anaesthetic. This fact is significant, because it means that the patient remains conscious. The patient can be questioned as to perceived neurological symptoms while the operation is proceeding.

Screw extractor tube 30 has a relatively small size—with an outside diameter of 18 to 19 mm and an inside diameter of 17 to 18 mm. An arthroscope is preferably placed through hollow interior 76 in order to visualize the pedicle screw head and surrounding region. A device intended to extract the pedicle screw must simultaneously be inserted through hollow interior 76. Those skilled in the art will thereby be informed that the device intended to remove the pedicle screw mut be very compact.

Figure 7:
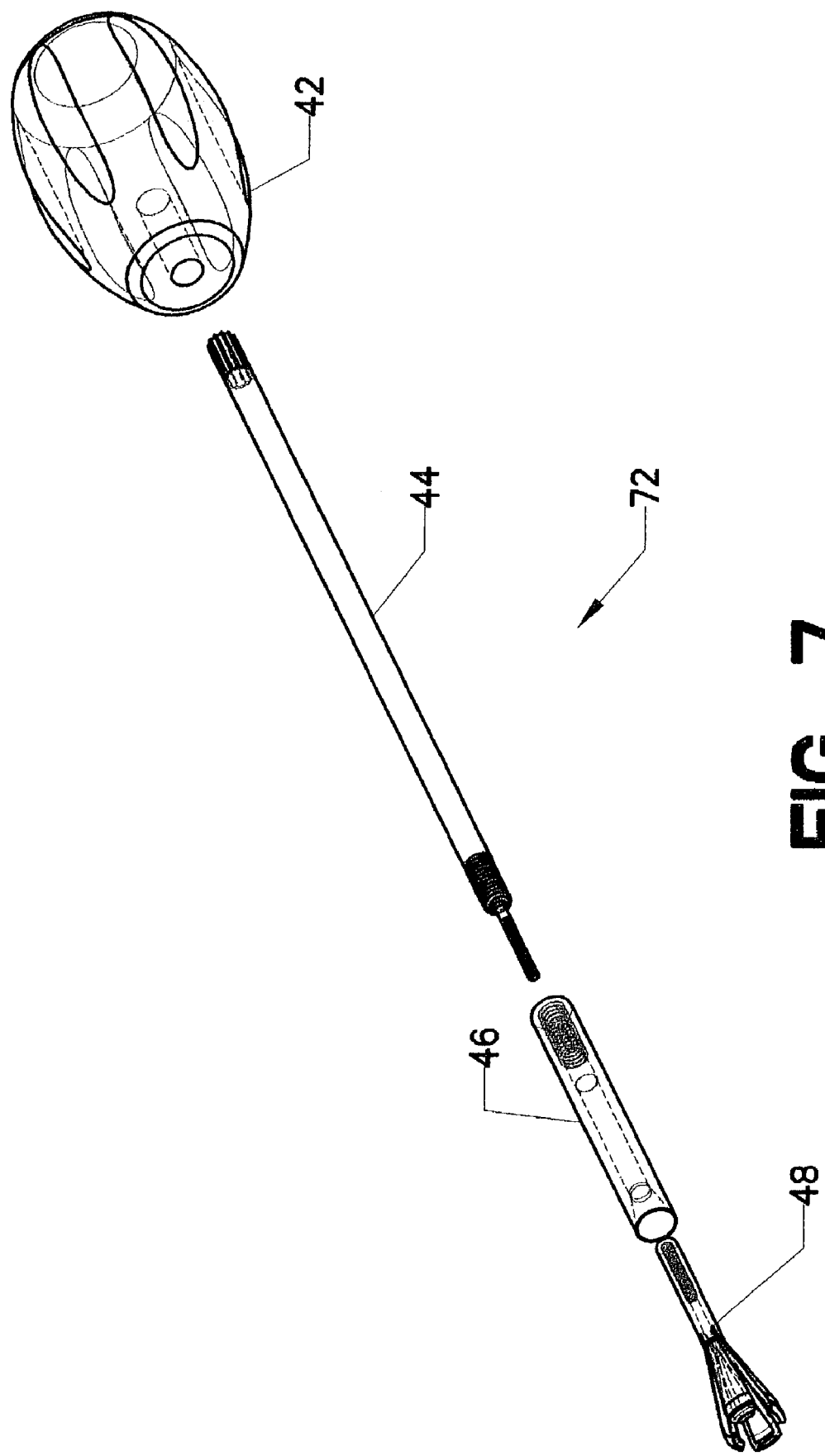
FIG. 7 is an isometric view, showing the components of an extraction tool.

FIG. 7 shows extraction tool 72, with its major components being separated to aid visualization. The major components are: handle 42, shaft 44, thread sleeve 46, and collet 48. As the assembly is a surgical instrument, it must be capable of undergoing sterilzation treatments in an autoclave. Shaft 44, thread sleeve 46, and collet 48 are preferably made of stainless steel. Handle 42 is preferably molded in a temperature—resistant polymer such as BAKELITE.

Figure 8:
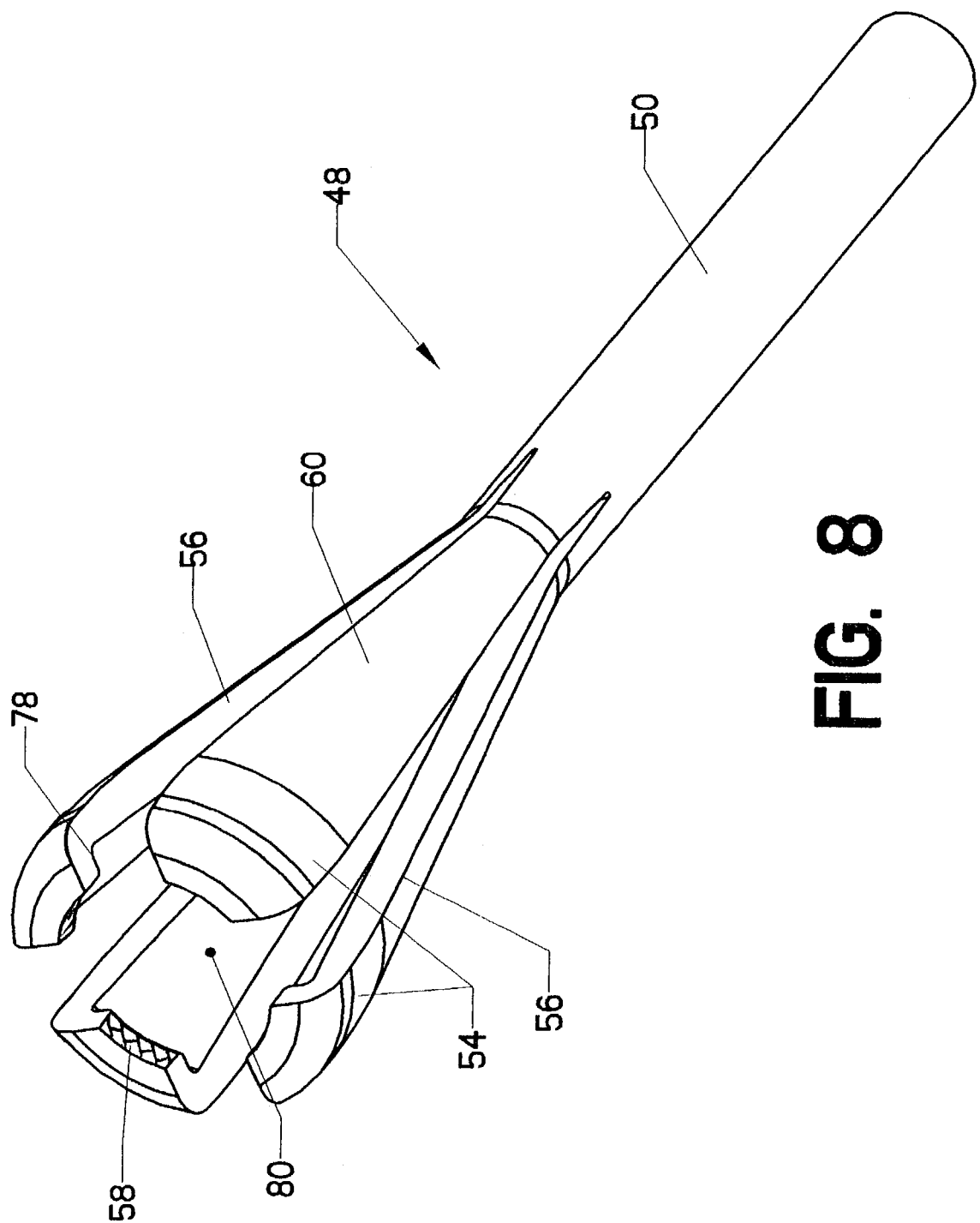
FIG. 8 is an isometric view, showing the details of the collet.

FIG. 8 shows collet 48 in greater detail. Its primary structure is mating cylinder 50. Four jaws 54 extend from the top of this structure (with "top" referring to the orientation as shown in the view). The jaws are separated from one another by four corresponding splits 56 (The number of jaws employed is not a critical feature, though a minimum of two are necessary). The reader will observe that the exterior surfaces of the four jaws 54 expand outward to form tapered journal 60 (which assumes the form of a truncated cone). The four jaws form a hollow interior denoted as screw head cavity 80. Undercuts 78 are formed just beneath each knurled surface 58. These features allow the four jaws 54 to grip a screw head which is angularly offset from the axial center of collet 48 (the importance of which will be made apparent in the following).

Figure 9:
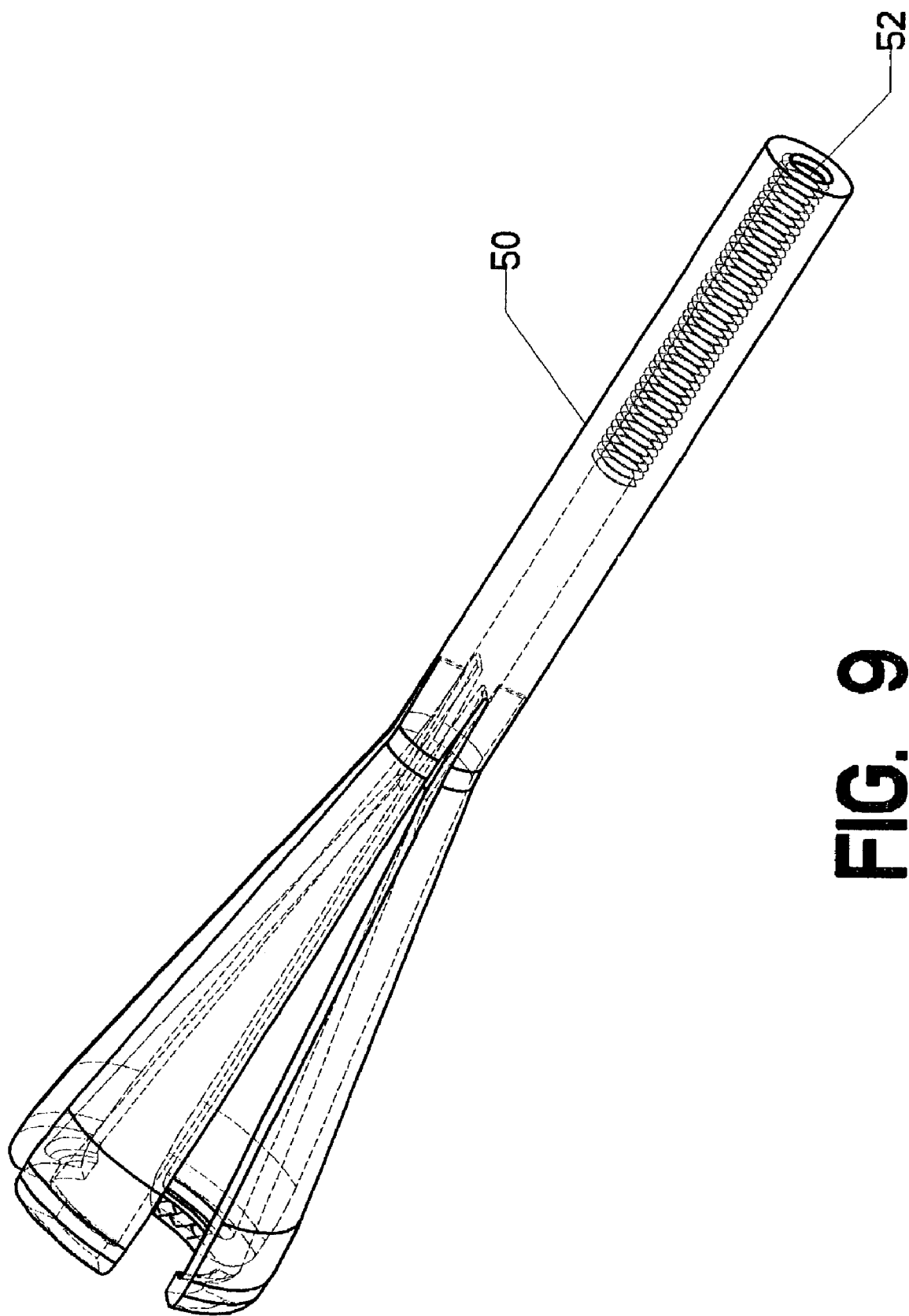
FIG. 9 is an isometric view, showing the details of the collet.

FIG. 9 depicts collet 48 from a different perspective. Insertion cylinder 50 is hollow. Threaded bore 52 extends into its interior—from the right hand side in the view as shown. It is not necessary to thread the full length of the hollow interior. The threaded portion indicated as threaded bore 52 may only extend for a portion of the available length. Those skilled in the art, having reviewed FIGS. 8 and 9, will realize that collet 48 generally assumes a form which is similar to an industrial collet as used in vertical milling machines (such as the Morse Taper or R-8 standards).

FIG. 10 depicts a portion of extraction tool 72, illustrating the interaction of the various components. Threaded journal 64 on shaft 44 threads into threaded bore 66 on thread sleeve 46. Both these threads are left hand threads, meaning that shaft 44 screws into thread sleeve 46 in a counterclockwise direction. Shaft 44 is typically screwed in until it stops, meaning that shaft 44 and thread sleeve 46 rotate as a unit during operation. In fact, shaft 44 and thread sleeve 46 could be made as one integral unit, with the use of two separate units being merely a choice of machining convenience (owing primarily to the need to machine and thread threaded journal 62).

Insertion cylinder 50 of collet 48 slides into straight bore 68 within thread sleeve 46. The diameters of the two cylindrical portions are closely matched so that they may slide relative to one another without wobbling.

Once shaft 44 is threaded into thread sleeve 46, threaded journal 62 extends into the interior of straight bore 68. When collet 48 is then pushed into straight bore 68, threaded bore 52 will engage threaded journal 62. Both these threads are left hand threads, meaning that if collet 48 is rotated in a counterclockwise direction, it will thread onto threaded journal 62. Those skilled in the art will therefore know that if shaft 44 and thread sleeve 46 are rotated in a counterclockwise direction (when viewed from the direction of the handle toward the collet), while collet 48 is held stationary, collet 48 will be drawn further into tapered sleeve 46 (drawn from left to right in the view as shown). As this process continues, tapered journal 60 will come to bear against tapered bore 70. As shaft 44 is rotated further, the jaws 54 of collet 48 will be squeezed together. This feature allows the device to grip a screw which is to be extracted.

Figure 10B:
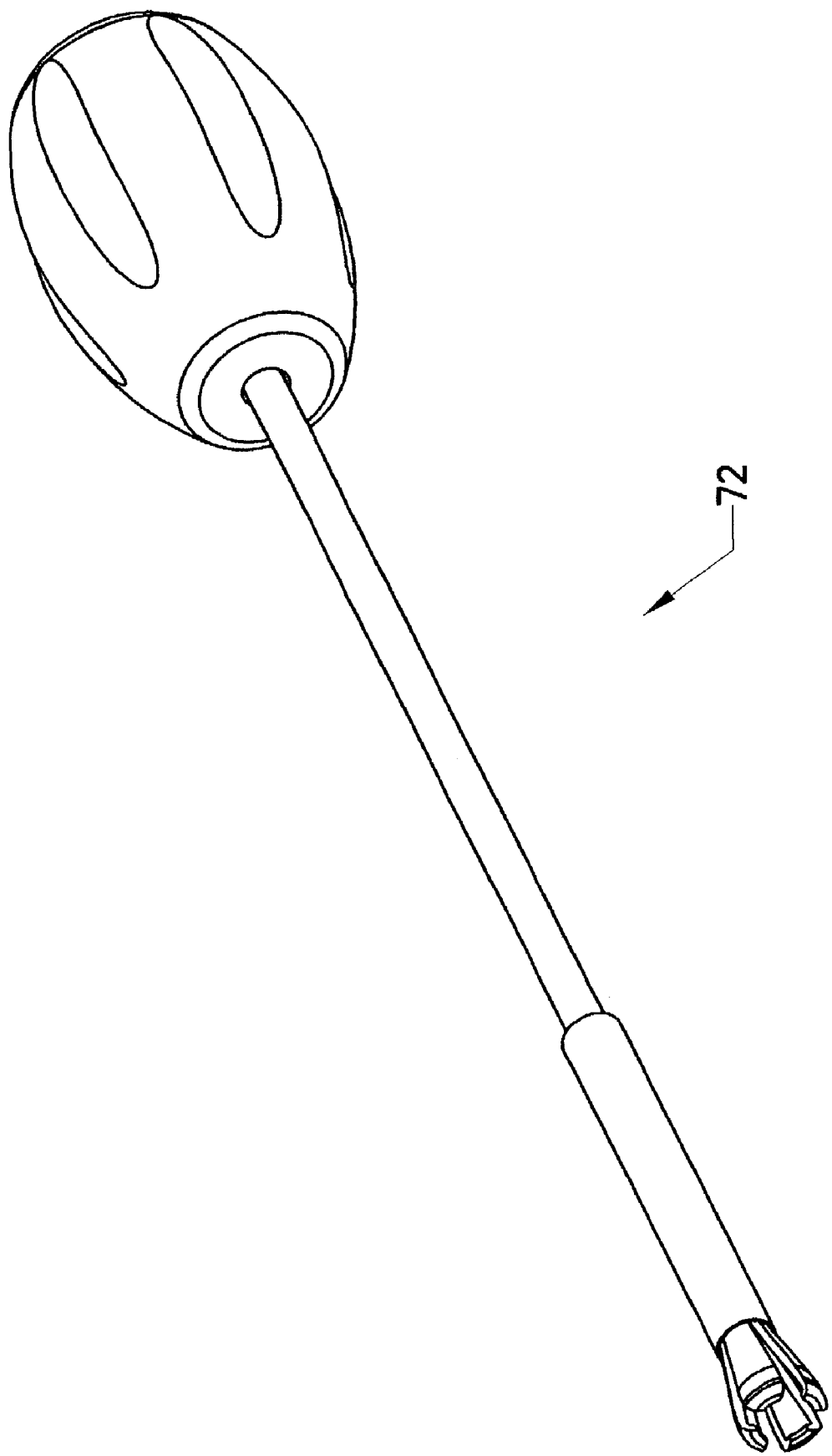
FIG. 10 is an isometric view, showing the interaction of the components comprising the extraction tool.
Figure 11:
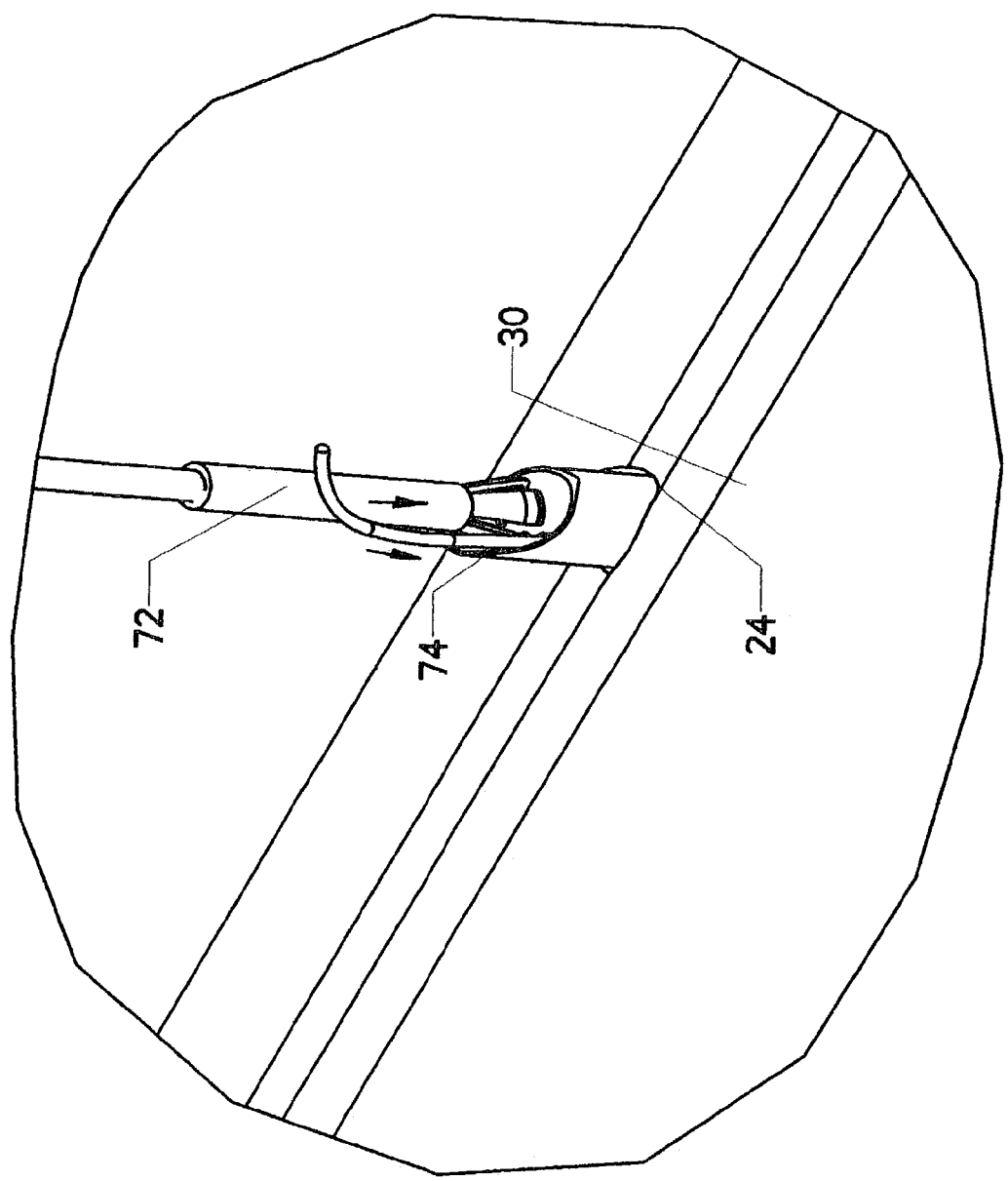
FIG. 11 is an isometric view, showing the insertion of an extraction tool.

FIG. 10B shows extraction tool 72 assembled and ready for use. FIG. 11 shows screw extractor tube 30 in position within small incision 24. Arthroscope 74 is fed down into screw extractor tube 30 to allow the surgeon to visualize the pedicle screw and surrounding structures. Extraction tool 72 is then inserted as shown.

FIGS. 12 through 15 illustrate the operation of the extraction tool. The reader should understand that pedicle screw 14 is fixed in a vertebra. Likewise, plate 12 is attached to the exterior of the same vertebra. Many other features—such as the incision, the screw extractor tube, the muscle structure, and various other anatomical features—are omitted from these views for purposes of visual clarity.

Figure 12:
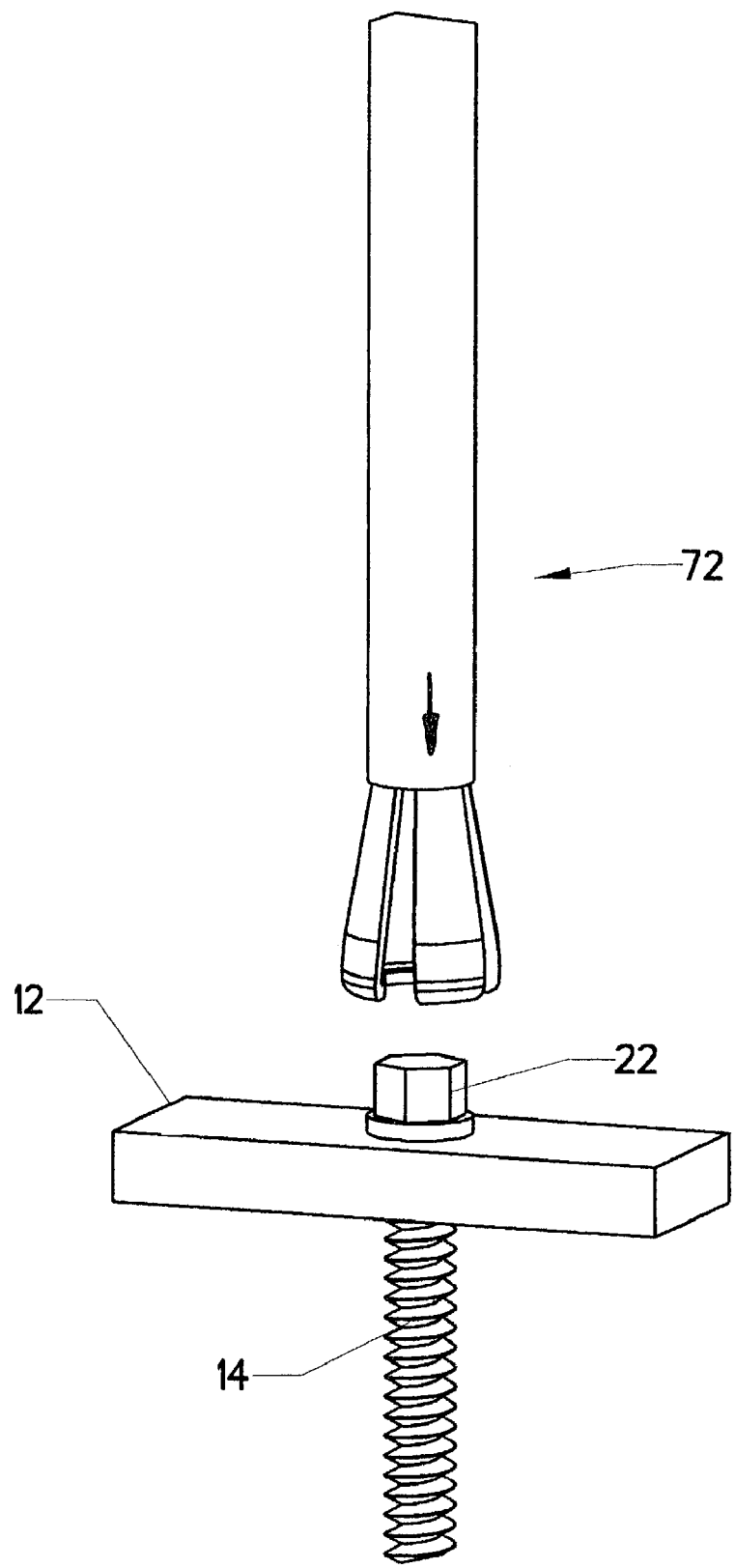
FIG. 12 is an isometric view, showing how the extraction tool attaches to a pedicle screw.
Figure 13:
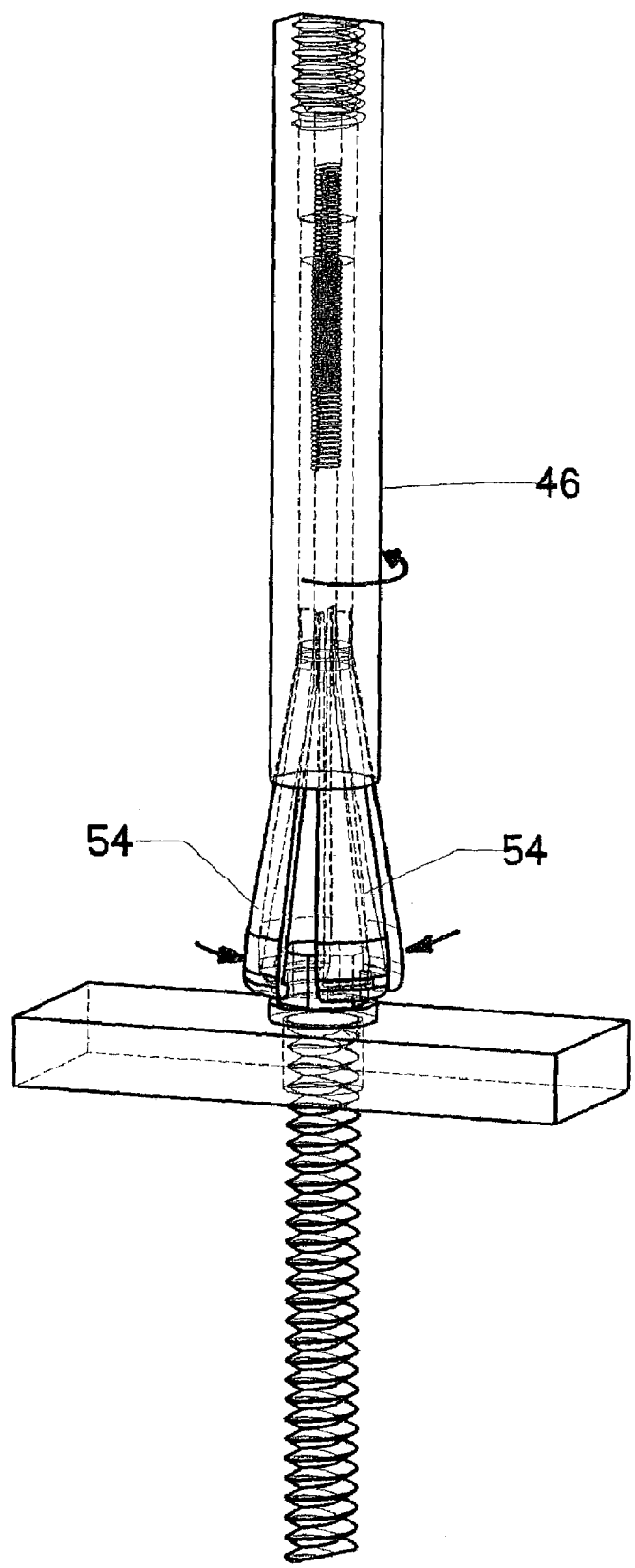
FIG. 13 is an isometric view, showing how the extraction tool attaches to a pedicle screw.

FIG. 12 shows extraction tool 72 descending toward screw head 22. In FIG. 13, jaws 54 have come to rest against screw head 22. At this point, the surgeon rotates shaft 44 in a counterclockwise direction (when viewed from the handle end). Thread sleeve 46, which is attached to shaft 44, also rotates in a counterclockwise direction. Knurled surfaces 58 on the inward facing sides of jaws 54 drag against screw head 22, which causes collet 48 to rotate more slowly than tapered sleeve 46. The result is that collet 48 is rotationally shifted with respect to thread sleeve 46 in a counterclockwise direction (when viewed from the handle end). The interaction of threaded bore 52 and threaded journal 62 then pulls tapered journal 60 against tapered bore 70, squeezing jaws 54 inward as shown. As jaws 54 are squeezed inward, knurled surfaces 58 grip the screw head more tightly. Those skilled in the art will realize that this is a mutually supporting process, meaning that as torque is applied to the device, it simultaneously applies torque to the screw head and squeezes the jaws more tightly into the screw head. Eventually, jaws 54 will be locked to the screw head.

Figure 14:
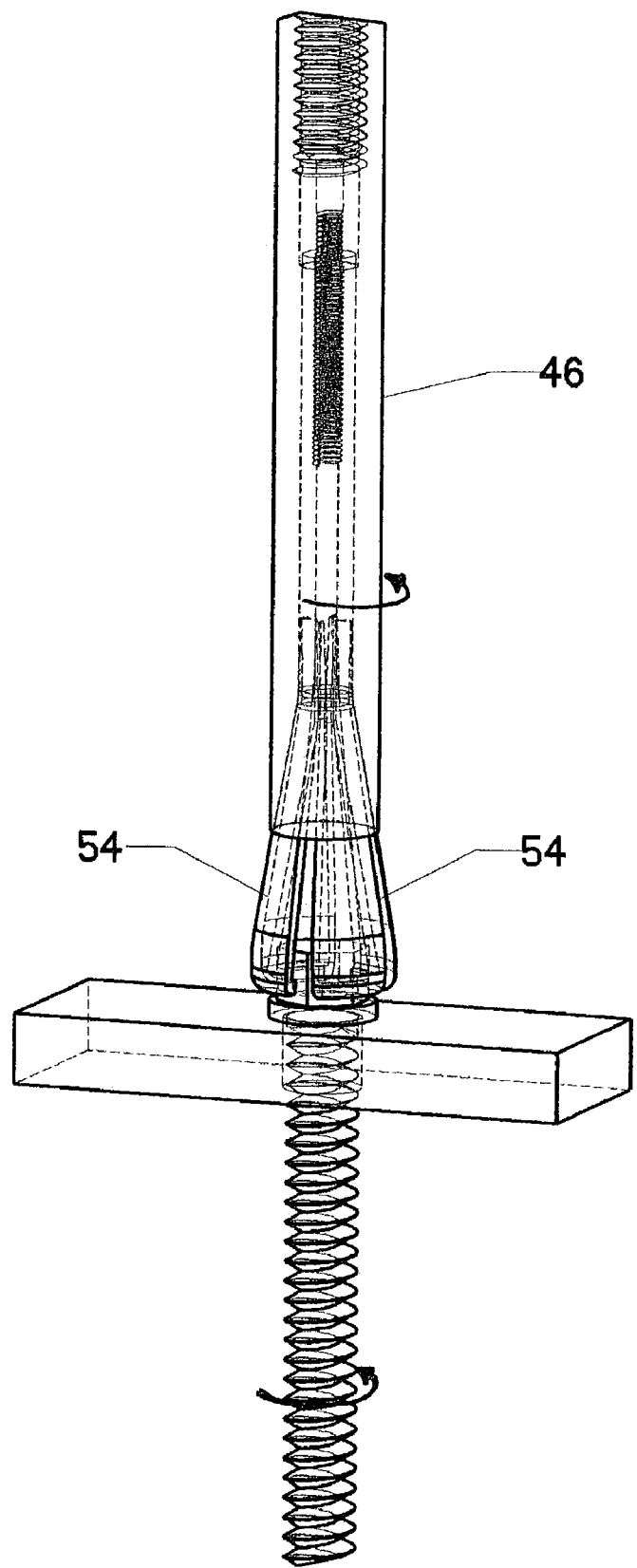
FIG. 14 is an isometric view, showing how the extraction tool unscrews a pedicle screw.
Figure 15:
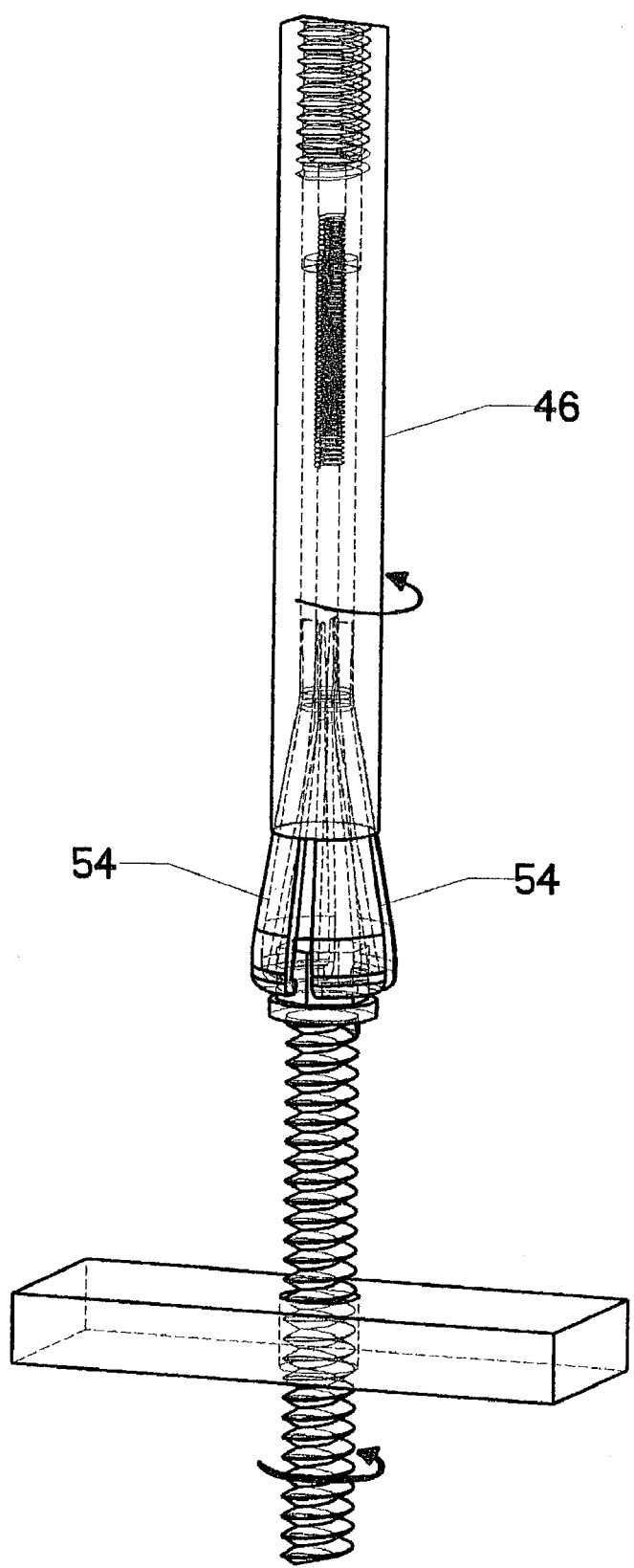
FIG. 15 is an isometric view, showing how the extraction tool backs out the pedicle screw.

FIG. 14 shows the assembly just after jaws 54 have locked to the screw head. As the surgeon continues rotating shaft 44 in a counterclockwise direction, pedicle screw 14 begins rotating in a counterclockwise direction—thereby backing it out of the vertebra. FIG. 15 shows this process as it continues, with pedicle screw 14 backing out.

Figure 16:
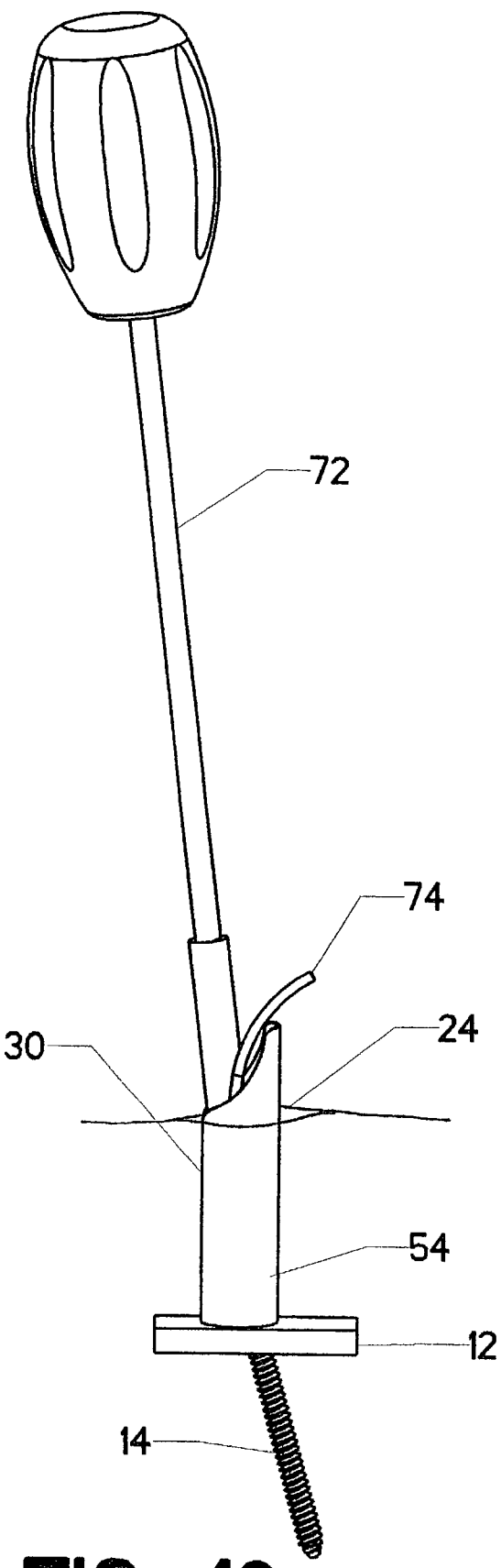
FIG. 16 is an isometric view, showing a complete view of the extraction tool in position.

FIG. 16 shows the application of extraction tool 72 with more of the surrounding elements illustrated. The reader will observe that screw extractor tube 30 is in place within incision 24. Both extraction tool 72 and arthroscope 74 are placed within the hollow interior of screw extractor tube 30. The reader will observe that the inventive process culminates in screw extractor tube 30 providing access from the patient's exterior to the head of pedicle screw 14.

This particular pedicle screw 14 was not inserted perpendicularly with respect to plate 12. Instead, it is angularly offset by approximately 15 degrees. This represents a realistic scenario, as it is often not possible to ideally place the orthopedic hardware—given variations in human anatomy.

Figure 17:
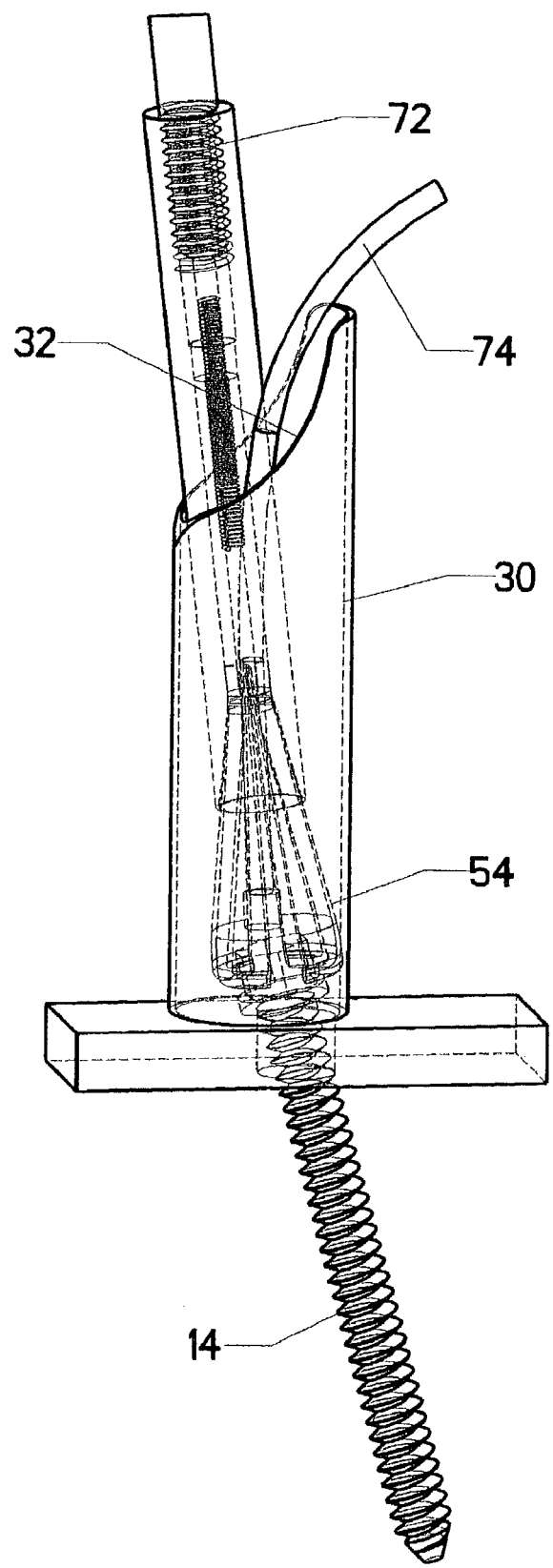
FIG. 17 is an isometric view, showing the extraction of an angularly offset pedicle screw.

FIG. 17 shows a closer view of the same assembly, with hidden lines being shown as well. The reader will observe that pedicle screw 14 is angularly offset from extraction tool 72. Jaws 54 are capable of engaging an angularly displaced screw head due to the presence of screw head cavity 80 and undercuts 78 on the jaws. Another feature is desirable to provide sufficient working room for the tool, however.

The side wall of screw extractor tube 30 opens into access cut 32. Once the surgeon has inserted screw extractor tube 30 into position, it is free to rotate. Thus, access cut 32 can be rotated to any desired angular position. The surgeon can visualize the position and angular offset of the pedicle screw by inspecting its head. For the scenario shown, extractor tube 30 has been rotated so that access cut 32 is facing the head of pedicle screw 14. With this orientation, the surgeon is able to orient extraction tool 72 more closely to the axial orientation of the pedicle screw. The surgeon then rotates shaft 44 in a counterclockwise direction (viewed from the handle end) to clamp jaws 54 on the screw head and begin extracting pedicle screw 14.

Figure 18:
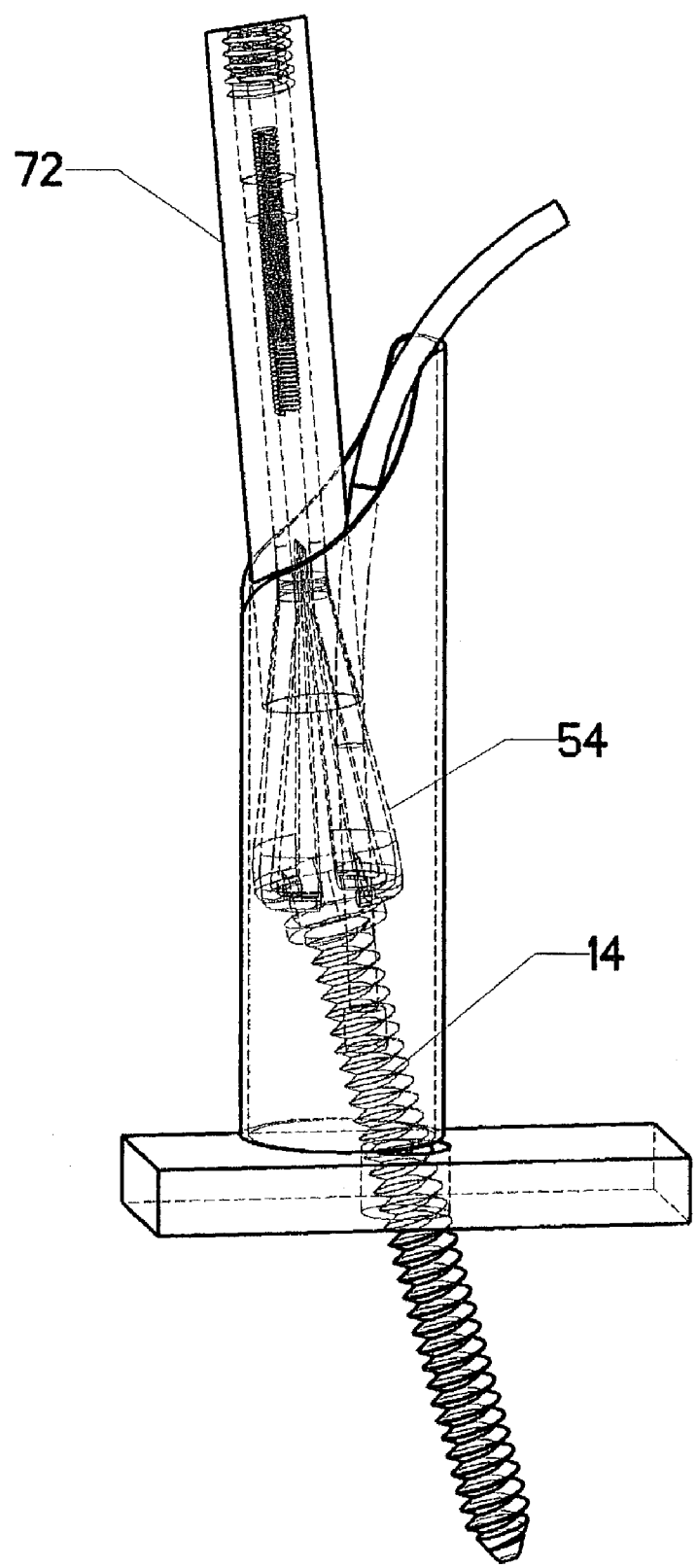
FIG. 18 is an isometric view, showing the extraction of an angularly offset pedicle screw.

FIG. 18 shows the extraction process midway through. As the surgeon continues rotating shaft 44 in a counterclockwise direction, pedicle screw 14 continues backing out of the vertebra Those skilled in the art will know that the angular offset between jaws 54 and the screw head continuously changes through each cycle of rotation, much in the fashion of a universal joint. Again, the shape of jaws 54—including the undercuts 78—means that the oscillation in the engagement angle between jaws 54 and the screw head is not a problem. The combination of torque and clamping force means that the engagement will remain secure.

Figure 19:
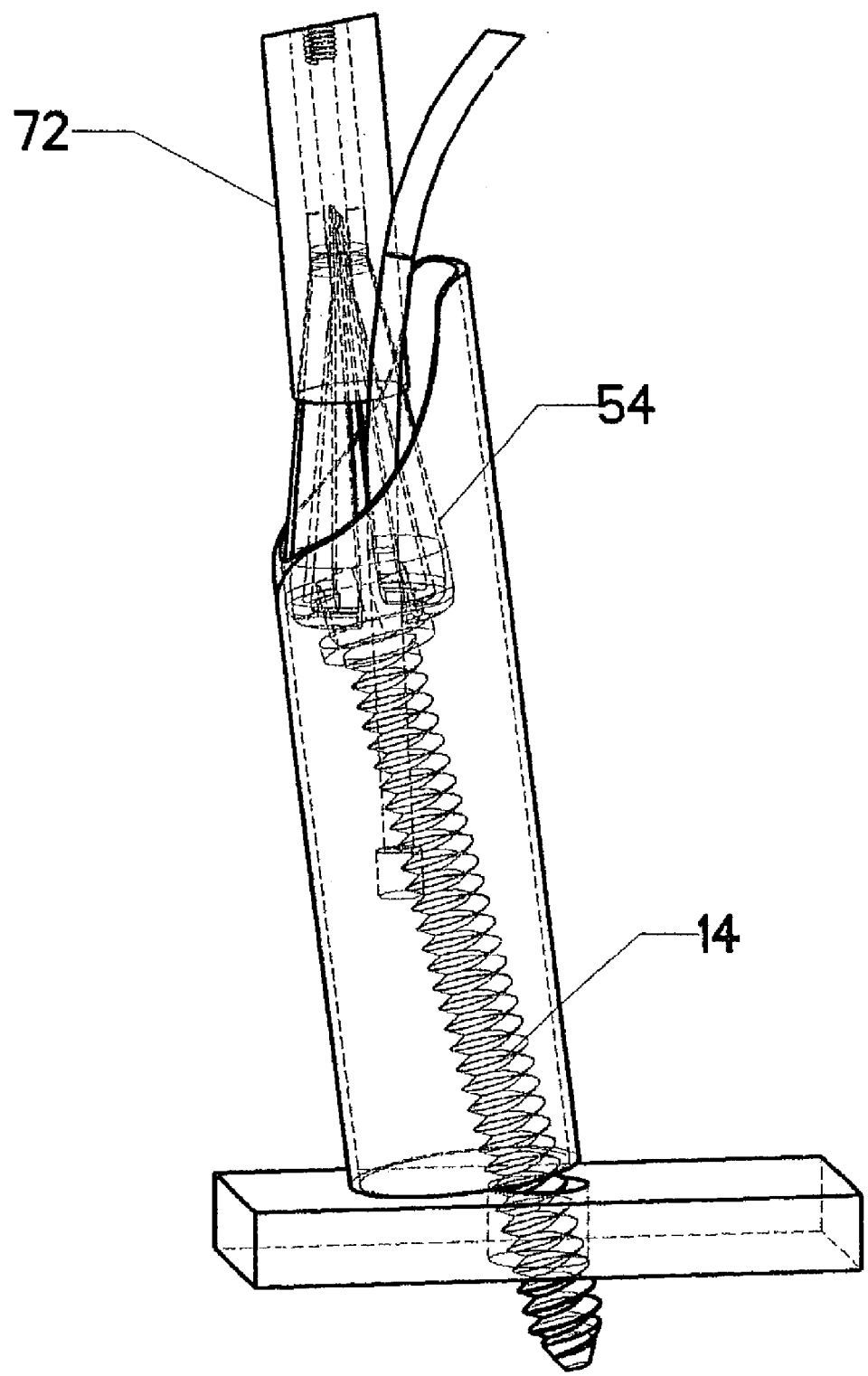
FIG. 19 is an isometric view, showing the extraction of an angularly offset pedicle screw.

FIG. 19 shows pedicle screw 14 when it is nearly free of the vertebra. It may be necessary for the surgeon to displace screw extractor tube 30 to a small extent in order to complete the extraction. The pliable nature of the structures surrounding screw extractor tube 30 allows such limited motion.

The reader will recall from the prior disclosure that the surgical procedures illustrated can be performed under a local anaesthetic. Thus, the patient is conscious and able to respond to questioning. If the pedicle screw illustrated was causing the compression of a nerve root in the installed position, one would expect the nerve to be decompressed once the position illustrated in FIG. 19 is reached. The surgeon can question the patient as to the neurological symptoms at this point. If the symptoms have resolved, then the surgeon can be confident that the pedicle screw was the source of the problem. If they have not resolved, then the pedicle screw is likely not the source of the problem. The surgeon can then elect to reinstall the screw and possibly move to another location to repeat the extraction cycle on another pedicle screw.

Once the pedicle screw is removed, screw extractor tube 30 continues to provide access for other finishing procedures. In some instances, the removal of the pedicle screw may leave small bone fragments behind. It may therefore be desirable to administer irrigation and suction to the area from which the pedicle screw was removed. The surgeon may elect to do so before removing screw extractor tube 30 and closing the incision. Screw extractor tube 30 can also provide access for other prior art procedures such as debridement, mechanical tissue removal, laser tissue destruction and removal, and arthroscopic visualization of internal structures.

Figure 20:
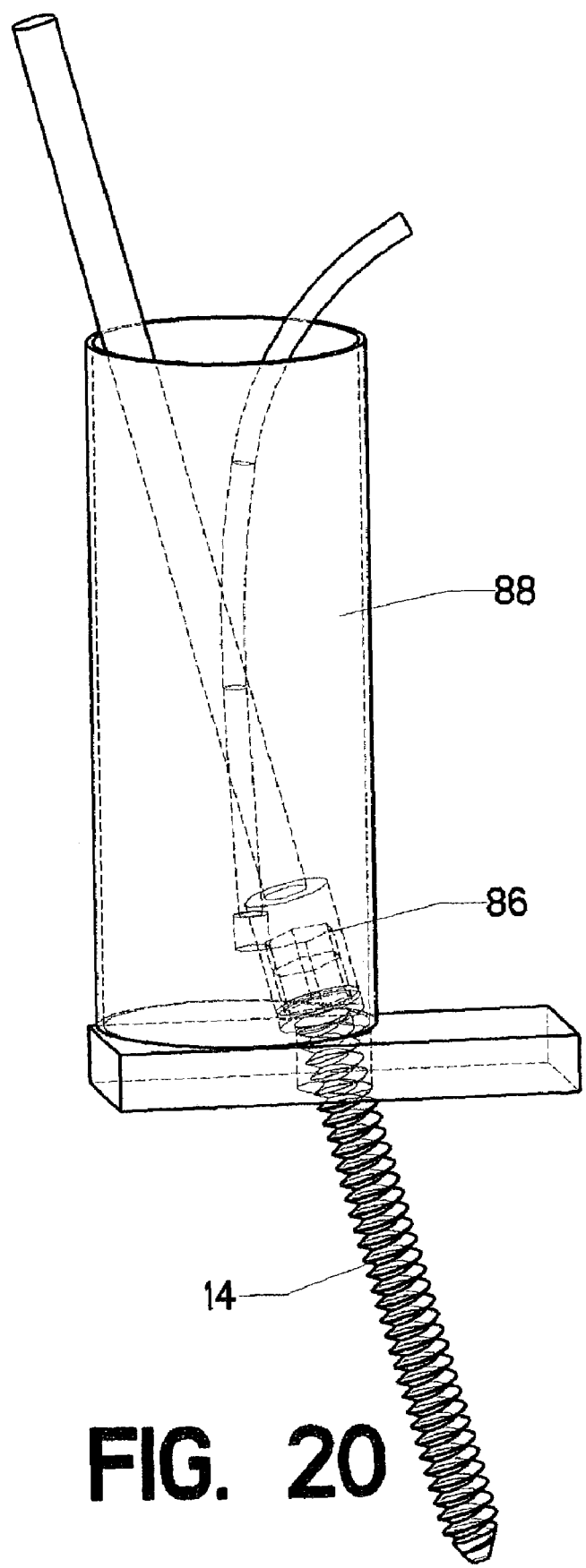
FIG. 20 is an isometric view, showing the extraction of an angularly offset pedicle screw with actor.

Those skilled in the art will appreciate that the use of extraction tool 72 and screw extractor tube 30 (incorporating access cut 32) allow these procedure to be performed through a very small incision. An open and much larger incision has been used traditionally. FIG. 20 provides some alternate tools. It does not represent a prior art technique, but it is helpful for purposes of comparison because the equipment illustrated in FIG. 20 represents what would be encountered if the presently disclosed techniques were practiced without the use of the specially shaped screw extractor tube 30 and extraction tool 72.

First, a socket extractor 86 is shown. This is a conventional wrench having a hexagonal female socket configured to engage the screw head. The shaft of such a tool must be angularly aligned with pedicle screw 14 (or very nearly so). Second, in the absence of an access cut, a much larger screw extractor tube must be used. This element is shown in FIG. 20 as large tube 88.

Having read the foregoing, those skilled in the art will realize that extraction tool 72 and screw extractor tube 30 are complementary to each other in the performance of the process disclosed. The shape shown for access cut 32 can be the subject of endless variations. The embodiment shown in FIG. 5 incorporates smooth and curved transitions which facilitate the use of the device and which minimize the risk of lacerating surrounding tissue. However, other simpler variations can also be used.

Figure 21:
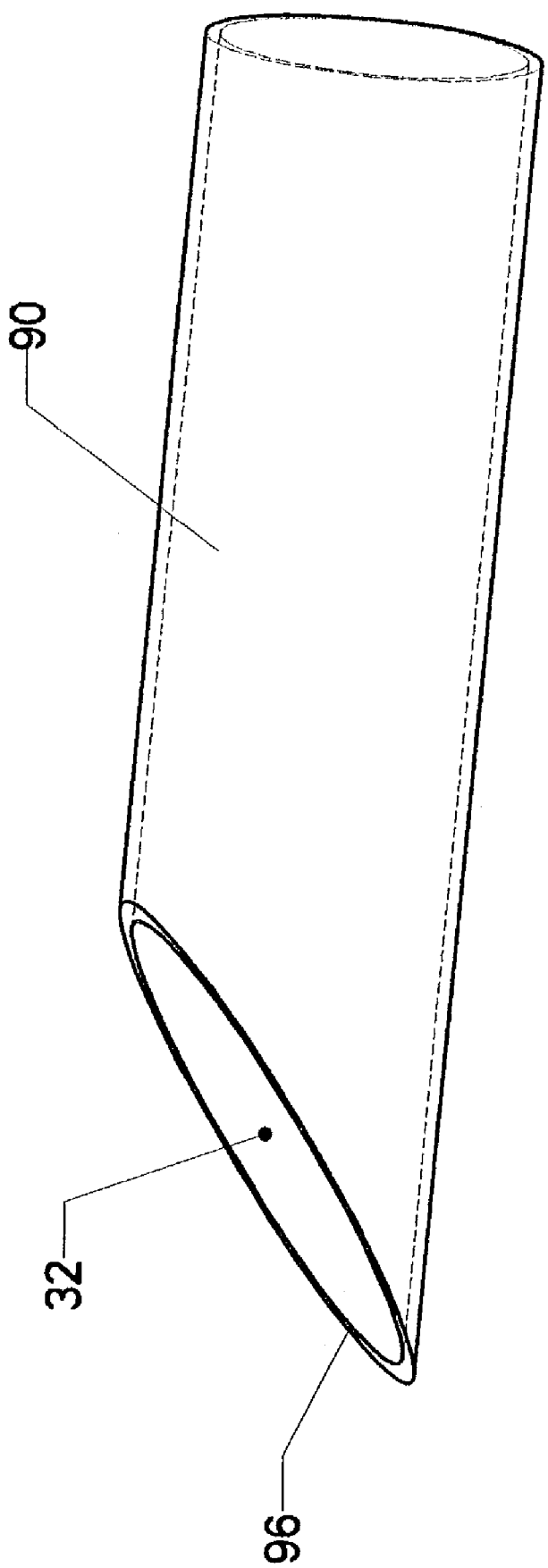
FIG. 21 is an isometric view, showing an alternate screw extractor tube.
Figure 22:
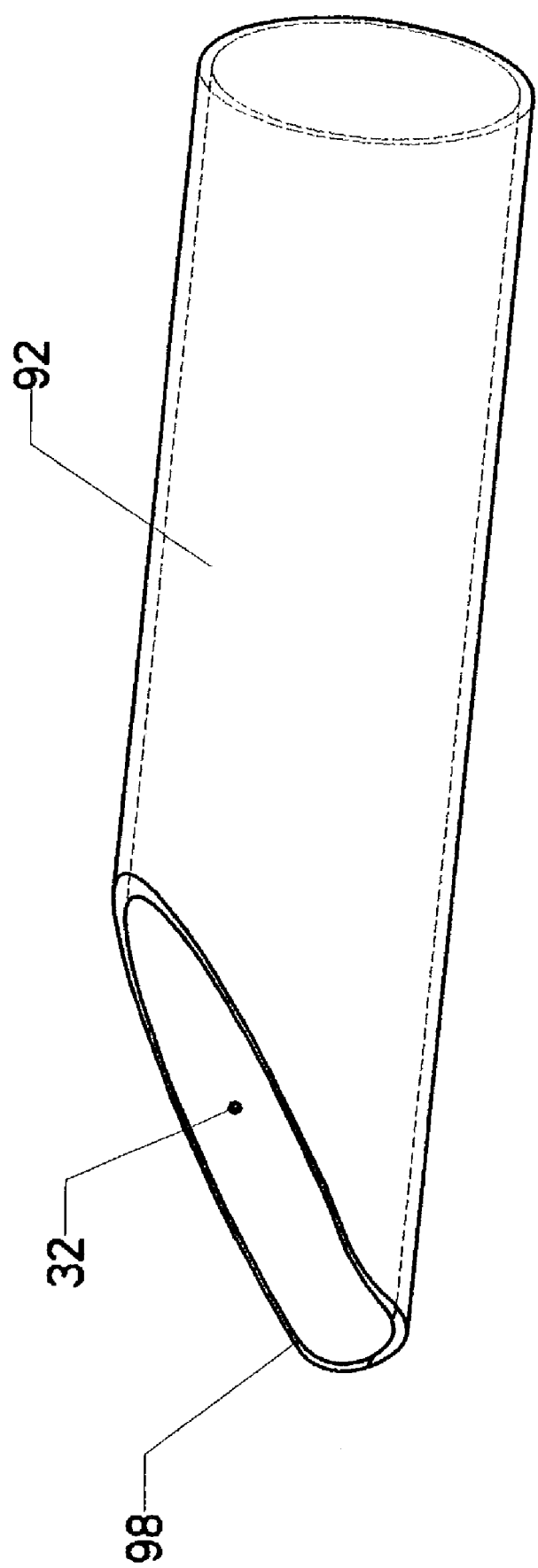
FIG. 22 is an isometric view, showing an alternate screw extractor tube.

FIG. 21 shows first alternate tube 90. In this version, access cut 32 assumes the form of an angled shear plane 98. FIG. 22 shows second alternate tube 92, wherein access cut 32 assumes the form of filleted shear plane 98. Filleted shear plane 98 incorporates a curved (or "filleted") edge to eliminate a sharp corner which might snag a tool.

Figure 23:
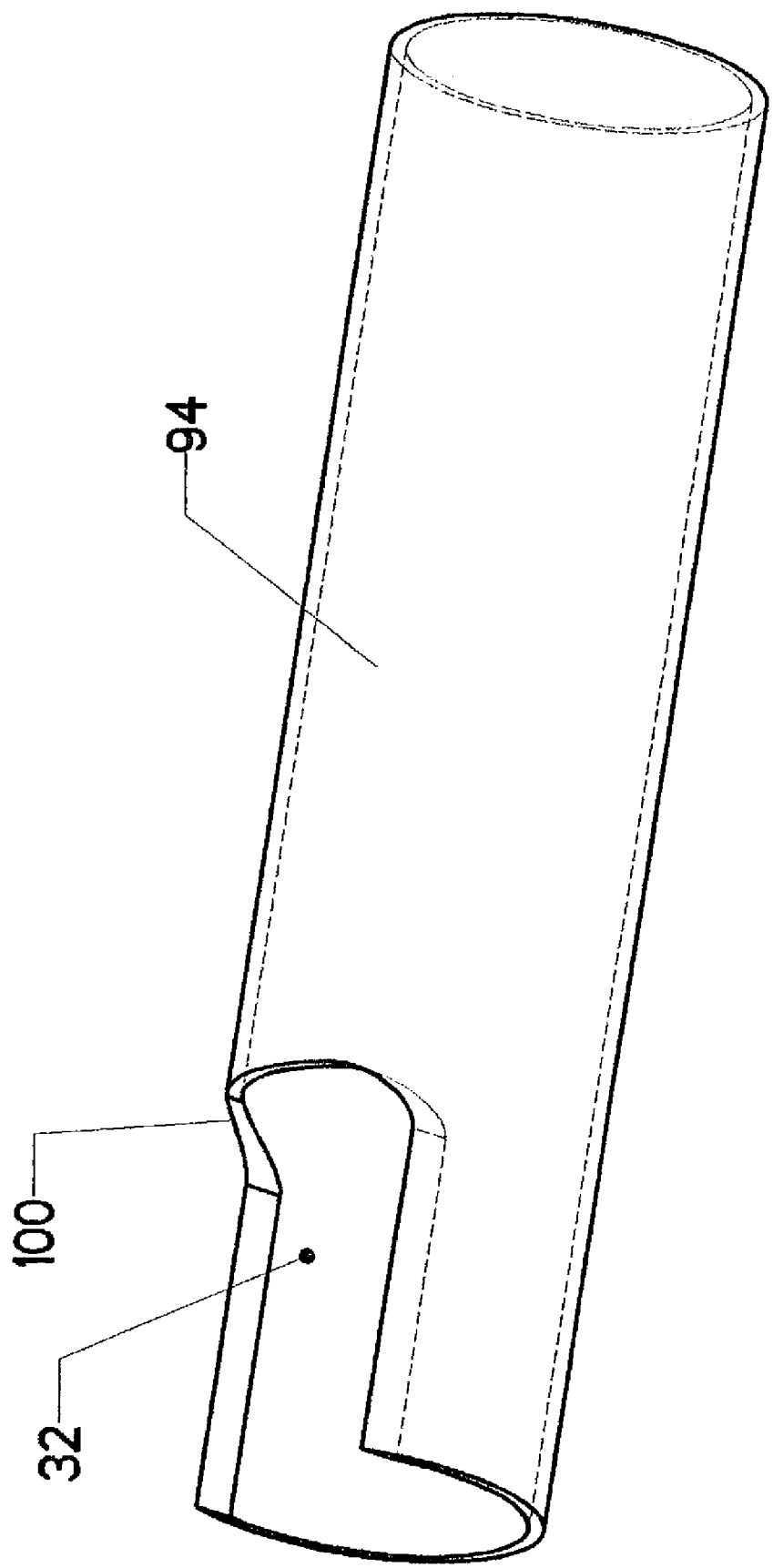
FIG. 23 is an isometric view, showing an alternate screw extractor tube.

FIG. 23 shows third alternate tube 94. In this embodiment, access cut 32 takes the form of notch 100, which is simply a relief cut into the side wall of the tube. All these embodiments of the screw extractor tube serve to illustrate the variations which are possible on the design of these elements. All these variations can be used to perform the present process. However, the embodiments shown in FIGS. 11 through 19 are preferred.

The preceding descriptions contain significant detail regarding the novel aspects of the present invention. They should not be construed, however, as limiting the scope of the invention but rather as providing illustrations of the preferred embodiments of the invention. Thus, the scope of the invention should be fixed by the following claims, rather than by the examples given.

Having described our invention, we claim:

1. A method for removing an orthopaedic fastener from a patient, said orthopaedic fastener having a threaded shaft with a right-hand thread and a screw head, said method comprising:
   a. making a small incision over said fastener;
   b. placing a guide wire into said incision and attaching said guide wire to said fastener;
   c. employing progressively larger dilator tubes over said guide wire to dilate said incision;
   d. placing a screw extractor tube over the largest of said progressively larger dilator tubes and into said incision;
   e. inserting an extractor tool into said screw extractor tube;
   f. using said extractor tool to grip said fastener and remove it through said screw extractor tube;
   g. removing said screw extractor tube from said incision; and
   h. closing said incision.

2. A method as recited in claim 1, further comprising inserting an arthroscope into said screw extractor tube in order to aid visualization.

3. A method as recited in claim 1, further comprising performing a secondary operation after said fastener has been removed but before said screw extractor tube is removed from said incision.

4. A method as recited in claim 3, wherein said secondary operation is selected from the list including debridement, mechanical tissue removal, laser tissue destruction and removal, and arthroscopic visualization of internal structures.

5. A method as recited in claim 1, further comprising evaluating said patient's neurological symptoms proximate said small incision, after said fastener is removed.

6. A method as recited in claim 1, wherein the step of employing progressively larger dilator tubes to dilate said incision includes placing successively larger in diameter dilator tubes into said incision while the smaller in diameter dilator tubes remain in said incision so that as said incision is successively dilated, each successive dilator tube telescopically receives its preceding dilator tube.

7. A method as recited in claim 1, wherein the step of employing progressively larger dilator tubes to dilate said incision includes placing a successively larger in diameter dilator tube into said incision while the immediately preceding dilator tube remains in said incision so that said larger in diameter dilator tube is telescopically received by said immediately preceding dilator tube, then removing said immediately preceding dilator tube.

8. A method as recited in claim 1, wherein said extractor tool includes
   a. a shaft, having a first end and a second end, wherein:
     i. said first end comprises a handle;
     ii. said second end opens into a hollow interior including a tapered bore proximate said second end;
     iii. said hollow interior includes a straight bore between said tapered bore and said handle;
     iv. said hollow interior includes a threaded protrusion lying within said straight bore, with said threaded protrusion having a left-hand thread;
   b. a collet, having a first end and a second end, wherein:
     i. said first end comprises an insertion cylinder sized to slidably fit within said straight bore within said shaft;
     ii. said first end opens into a threaded bore, with said threaded bore having a left-hand thread, and being threaded onto said threaded protrusion within said hollow interior of said shaft; and
     iii. said second end comprises at least two jaws, forming therebetween a screw head cavity, wherein the exterior surface of said at least two jaws forms a tapered journal shaped to bear against said tapered bore, so that when said at least two jaws are placed over said screw head, and when said shaft is then rotated in a counterclockwise direction when viewed from said first end of said shaft toward said second end of said shaft, said jaws will bear against said screw head, thereby impeding the rotation of said collet and causing said shaft to rotate in a counterclockwise direction relative to said collet, whereby said left-hand threaded engagement between said threaded bore in said collet and said threaded protrusion within said hollow interior of said shaft will draw said collet further into said hollow interior, causing said tapered journal to bear against said tapered bore so as to squeeze said at least two jaws inward, so that said screw head is gripped tightly, whereby continuing counterclockwise rotation of said shaft will back out said orthopedic screw.

9. A method as recited in claim 8, further comprising inserting an arthroscope into said screw extractor tube in order to aid visualization.

10. A method as recited in claim 8, further comprising performing a secondary operation after said fastener has been removed but before said screw extractor tube is removed from said incision.

11. A method as recited in claim 8, wherein said secondary operation is selected from the list including debridement, mechanical tissue removal, laser tissue destruction and removal, and arthroscopic visualization of internal structures.

12. A method as recited in claim 8, further comprising evaluating said patient's neurological symptoms proximate said small incision, after said fastener is removed.

13. A method as recited in claim 8, wherein the step of employing progressively larger dilator tubes to dilate said incision includes placing successively larger in diameter dilator tubes into said incision while the smaller in diameter dilator tubes remain in said incision so that as said incision is successively dilated, each successive dilator tube telescopically receives its preceding dilator tube.

14. A method as recited in claim 8, wherein the step of employing progressively larger dilator tubes to dilate said incision includes placing a successively larger in diameter dilator tube into said incision while the immediately preceding dilator tube remains in said incision so that said larger in diameter dilator tube is telescopically received by said immediately preceding dilator tube, then removing said immediately preceding dilator tube.

* * * * *